United States Patent
Larsen et al.

(10) Patent No.: US 11,802,114 B2
(45) Date of Patent: Oct. 31, 2023

(54) COMPOUNDS AND METHODS FOR DETECTION OF SUPEROXIDE

(71) Applicant: Promega Corporation, Madison, WI (US)

(72) Inventors: Matthew A. Larsen, Madison, WI (US); Hui Wang, Madison, WI (US); Wenhui Zhou, Verona, WI (US); Peter Hofsteen, Madison, WI (US); Jolanta Vidugiriene, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 17/870,509

(22) Filed: Jul. 21, 2022

(65) Prior Publication Data

US 2023/0106144 A1 Apr. 6, 2023

Related U.S. Application Data

(60) Provisional application No. 63/224,087, filed on Jul. 21, 2021.

(51) Int. Cl.
| | | |
|---|---|---|
| *C07D 277/82* | (2006.01) | |
| *C07D 277/68* | (2006.01) | |
| *C07F 9/54* | (2006.01) | |

(52) U.S. Cl.
CPC ......... *C07D 277/82* (2013.01); *C07D 277/68* (2013.01); *C07F 9/5442* (2013.01)

(58) Field of Classification Search
None
See application file for complete search history.

(56) References Cited

U.S. PATENT DOCUMENTS 8,828,678 B2 * 9/2014 Szczepanik .......... C07D 493/10
544/149
2013/0287699 A1 10/2013 Chang et al.

FOREIGN PATENT DOCUMENTS

| WO | WO 2006/130551 | 12/2006 |
|---|---|---|
| WO | WO 2011/112966 | 9/2011 |
| WO | WO 2011/133800 | 10/2011 |

OTHER PUBLICATIONS

International Search Report and Written Opinion for PCT/US2022/037885. dated Nov. 7, 2022. 11 pages.
Kalyanaraman et al., Pitfalls of Reactive Oxygen Species (ROS) Measurements by Fluorescent Probes and Mitochondrial Superoxide Determination Using MitoSOX in Biological Systems, Biological magnetic Resonance 34, Chapter 2, pp. 7-9.
Polster et al., Use of potentiometric fluorophores in the measurement of mitochondrial reactive oxygen species. Methods Enzymol. 2014;547:225-50.
Robinson et al., Selective fluorescent imaging of superoxide in vivo using ethidium-based probes. Proc Natl Acad Sci U S A. Oct. 10, 2006;103(41):15038-43.
Xiao et al., Are Hydroethidine-Based Probes Reliable for Reactive Oxygen Species Detection? Antioxid Redox Signal. Aug. 1, 2019;31(4):359-367.
Zhao et al., Detection and characterization of the product of hydroethidine and intracellular superoxide by HPLC and limitations of fluorescence. Proc Natl Acad Sci U S A. Apr. 19, 2005;102(16):5727-5732.
Zielonka et al., Hydroethidine- and MitoSOX-derived red fluorescence is not a reliable indicator of intracellular superoxide formation: another inconvenient truth. Free Radic Biol Med. Apr. 15, 2010;48(8):983-1001.
Zielonka et al., On the use of L-012, a luminol-based chemiluminescent probe, for detecting superoxide and identifying inhibitors of NADPH oxidase: a reevaluation. Free Radic Biol Med. Dec. 2013;65:1310-1314.

* cited by examiner

*Primary Examiner* — Samantha L Shterengarts
(74) *Attorney, Agent, or Firm* — CASIMIR JONES, S.C.; Anne M. Reynolds

(57) ABSTRACT

Disclosed herein are compounds that can be used to selectively detect superoxide in samples. Also disclosed herein are compositions comprising the compounds and methods of detecting superoxide using the compounds.

20 Claims, 6 Drawing Sheets

FIGS. 1A-1B
FIG. 1A
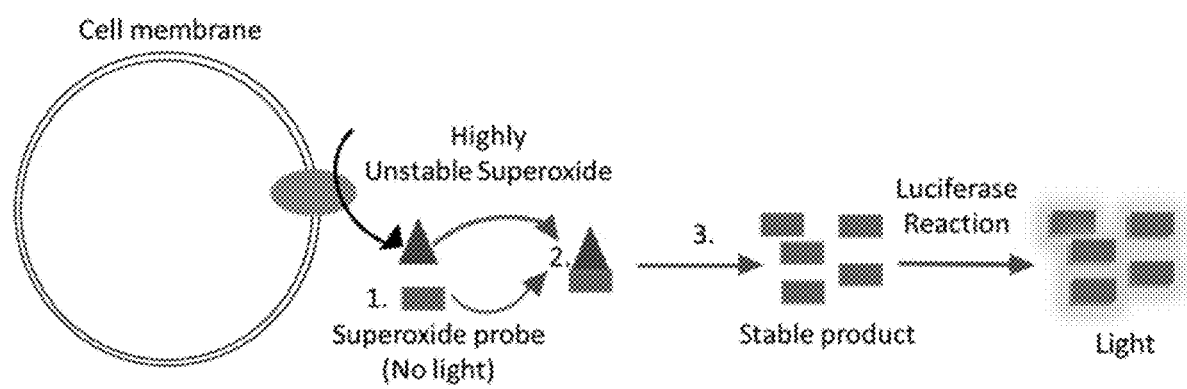
FIG. 1B
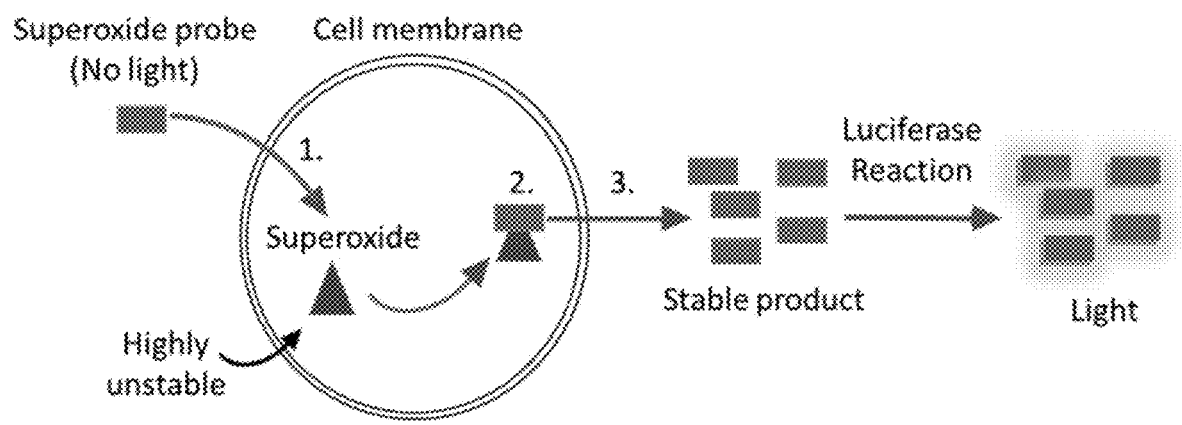

FIGS. 6A-6B
FIG. 6A
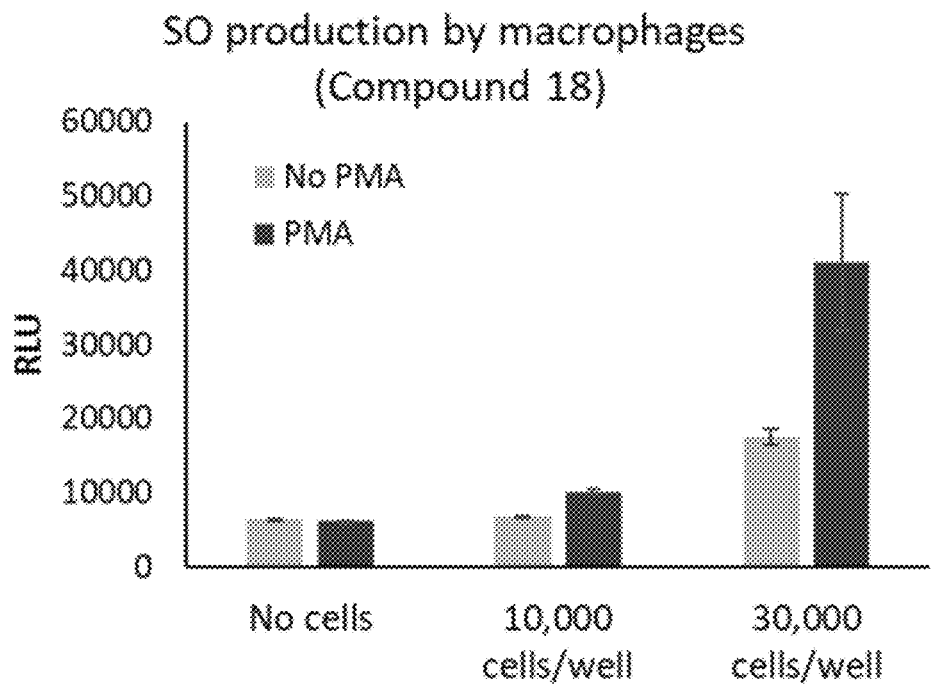
FIG. 6B
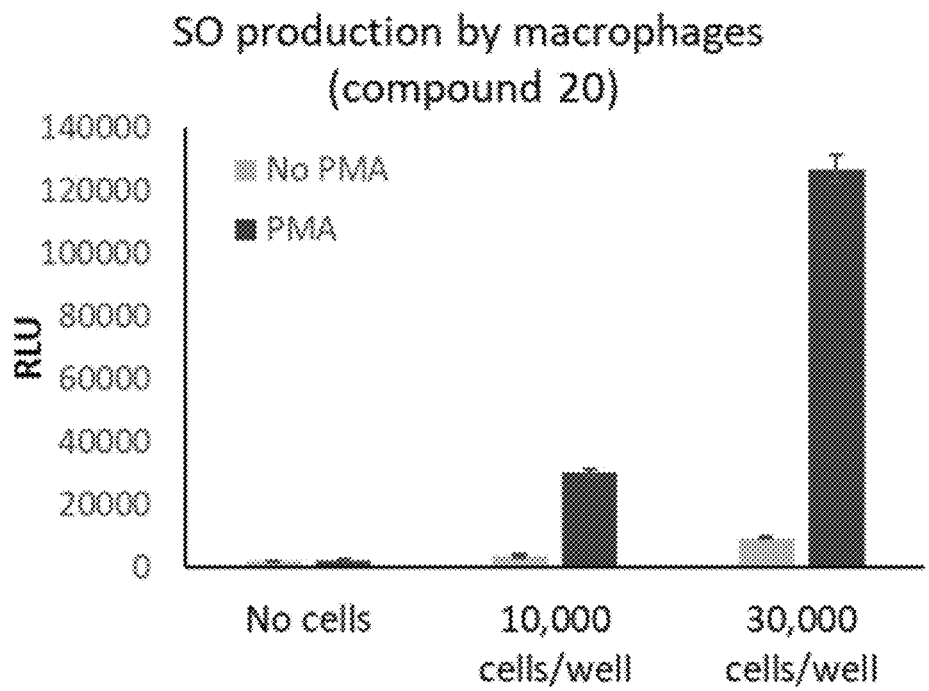

COMPOUNDS AND METHODS FOR DETECTION OF SUPEROXIDE

CROSS-REFERENCE TO RELATED APPLICATIONS

This application claims priority to and the benefit of U.S. Provisional Patent Application No. 63/224,087, filed on Jul. 21, 2021, which is incorporated herein by reference in its entirety.

TECHNICAL FIELD

Disclosed herein are compounds that can be used to selectively detect superoxide in samples. Also disclosed herein are compositions comprising the compounds and methods of detecting superoxide using the compounds.

BACKGROUND

Superoxide is a highly unstable and tightly regulated reactive oxygen species that is central to cellular homeostasis. Dysregulation of superoxide can result in disease states including cardiovascular disease, cancer, atherosclerosis, hypertension, diabetes, and endothelial dysfunction. Direct and specific detection of superoxide in a cellular context is highly desirable. Due to the short-lived residence time (half-life of $10^{-6}$ to $10^{-9}$ seconds depending on superoxide dismutase availability), it is inherently difficult to accurately measure superoxide in cells. Current technologies to detect superoxide rely on chemiluminescent and fluorescent probes that often lack sufficient selectivity. For example, hydroethidine has a propensity to undergo autoxidation and other non-superoxide specific oxidation reactions, which lead to production of fluorescent products that have similar emission spectra as that of the superoxide-specific product. Another compound, luminol, can also react with reactive oxygen species other than superoxide, and one of the reactive intermediates in luminol's oxidation pathway can itself generate superoxide, leading to potential overestimation of the amount of superoxide present.

SUMMARY

In one aspect, the disclosure provides a compound of formula (II):

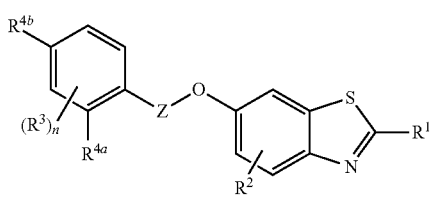

or a salt thereof, wherein:
$R^1$ is selected from —CN and

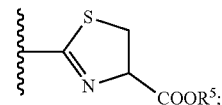

$R^2$ is selected from hydrogen and halo;
n is 0, 1, 2, or 3; and
each $R^3$ is independently selected from $C_1$-$C_4$ alkyl, $C_1$-$C_4$ alkoxy, —OC(O)-$C_1$-$C_4$ alkyl, hydroxy, amino, and a group -Linker-X, wherein X is a targeting moiety;
one of $R^{4a}$ and $R^{4b}$ is hydroxy or —OC(O)-$C_1$-$C_4$ alkyl, and the other is hydrogen or a group -Linker-X, wherein X is a targeting moiety;
$R^5$ is selected from hydrogen and $C_1$-$C_4$ alkyl;
Z is a bond or a group of formula

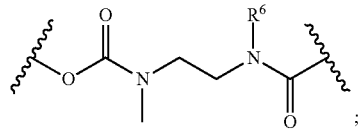

and
$R^6$ is selected from $C_1$-$C_4$ alkyl and a group -Linker-Y, wherein Y is a targeting moiety.

In some embodiments, Z is a group of formula

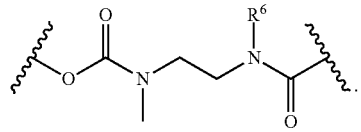

In some embodiments, $R^6$ is methyl. In some embodiments, $R^6$ is a group -Linker-Y, wherein Y is a mitochondrial targeting moiety. In some embodiments, Y is a triphenylphosphonium moiety.

In some embodiments, n is 1 and $R^3$ is selected from —OC(O)CH$_3$ and hydroxy.

In some embodiments, $R^{4a}$ is hydrogen and $R^{4b}$ is hydroxy or —OC(O)CH$_3$.

In some embodiments, the compound is a compound of formula (I):

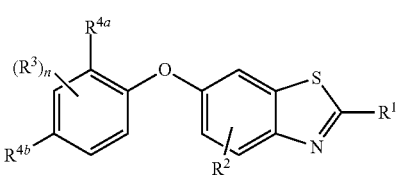

or a salt thereof, wherein:
$R^1$ is selected from —CN and

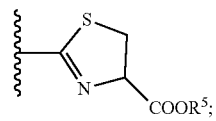

$R^2$ is selected from hydrogen and halo;
n is 0, 1, 2, or 3; and
each $R^3$ is independently selected from $C_1$-$C_4$ alkyl, $C_1$-$C_4$ alkoxy, amino, and a group -Linker-X, wherein X is a targeting moiety;

one of $R^{4a}$ and $R^{4b}$ is hydroxy and the other is hydrogen or a group -Linker-X, wherein X is a targeting moiety; and $R^5$ is selected from hydrogen and $C_1$-$C_4$ alkyl.

In some embodiments, $R^1$ is —CN. In some embodiments, $R^1$ is

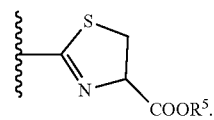

In some embodiments, $R^5$ is selected from hydrogen and methyl.

In some embodiments, $R^2$ is hydrogen. In some embodiments, $R^2$ is fluoro.

In some embodiments, the compound is a compound of formula (Ia):

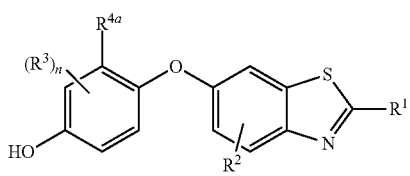

(Ia)

or a salt thereof, wherein $R^{4a}$ is hydrogen or a group -Linker-X, wherein X is a targeting moiety.

In some embodiments, the compound is a compound of formula (Ib):

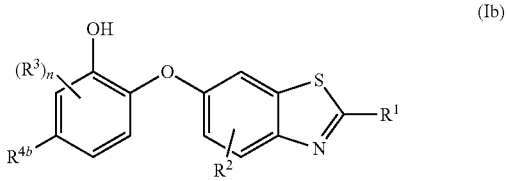

(Ib)

or a salt thereof, wherein $R^{4b}$ is hydrogen or a group -Linker-X, wherein X is a targeting moiety.

In some embodiments, n is 0, 1, or 2, and each $R^3$ is independently selected from $C_1$-$C_4$ alkyl, $C_1$-$C_4$ alkoxy, —OC(O)-$C_1$-$C_4$ alkyl, and hydroxy. In some embodiments, n is 0, 1, or 2, and each $R^3$ is independently selected from $C_1$-$C_4$ alkyl and $C_1$-$C_4$ alkoxy. In some embodiments, at least one $R^3$ is a group -Linker-X, wherein X is a mitochondrial targeting moiety. In some embodiments, X is a triphenylphosphonium moiety.

In some embodiments, the compound is selected from the group consisting of:

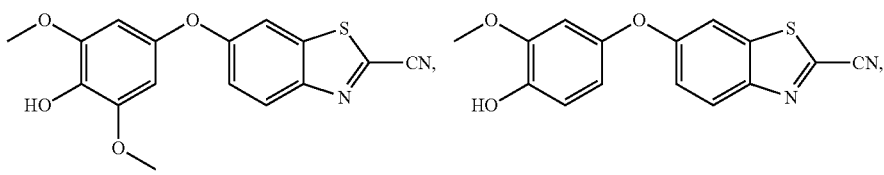

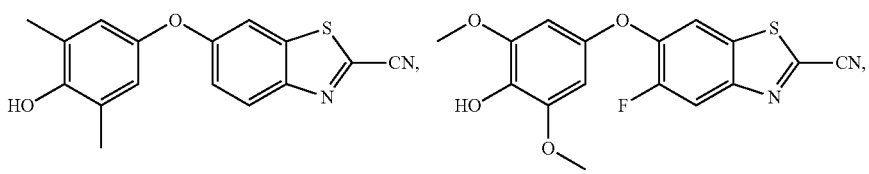

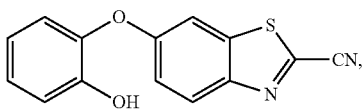

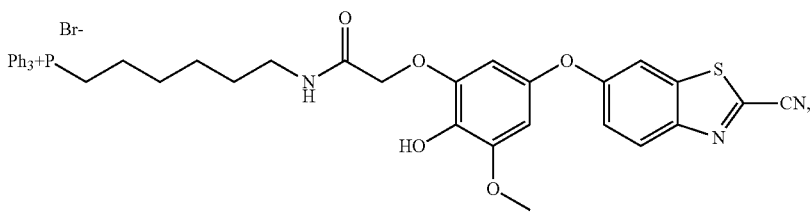

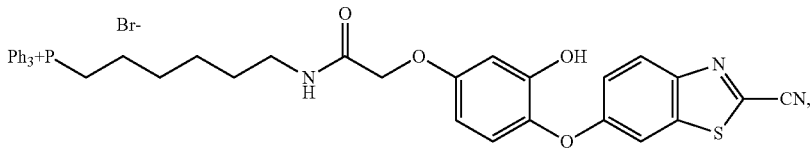

-continued
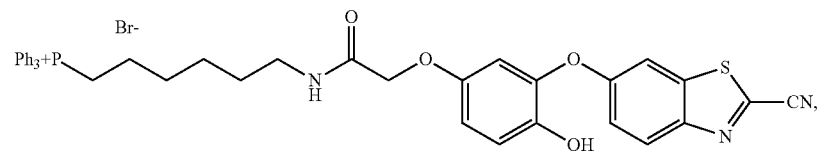
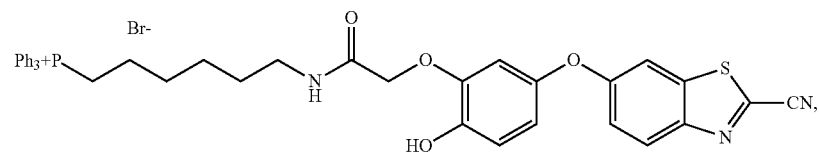
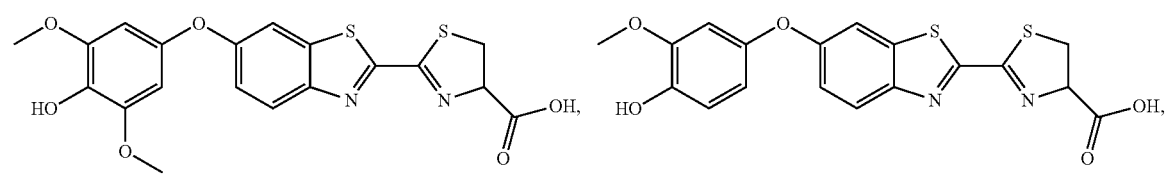
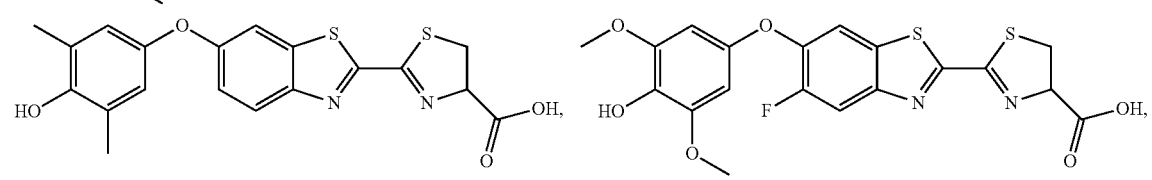
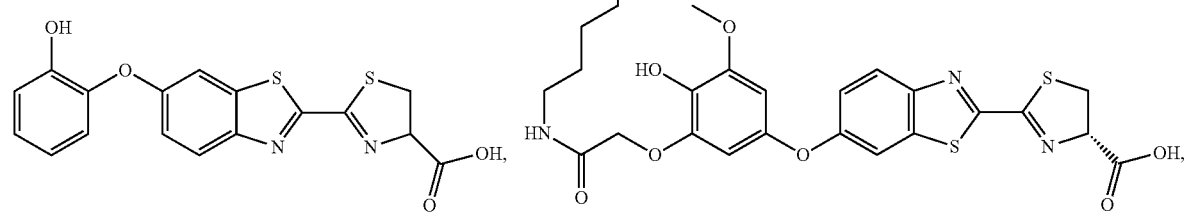
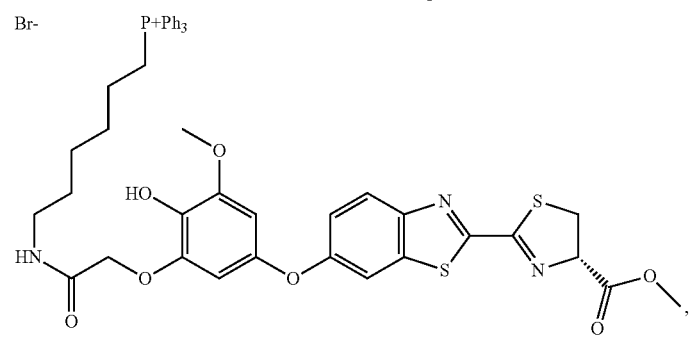
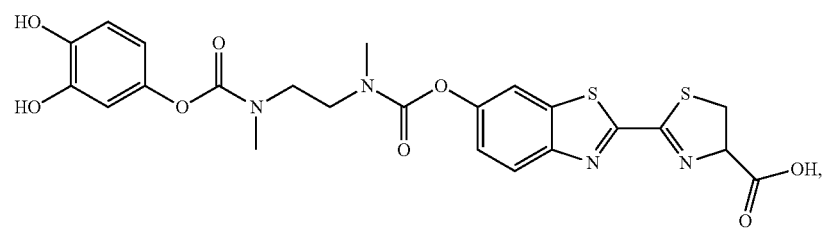

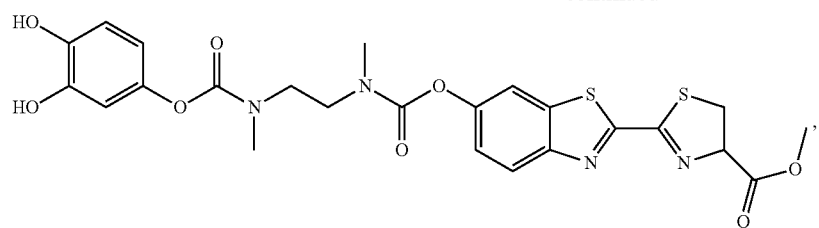
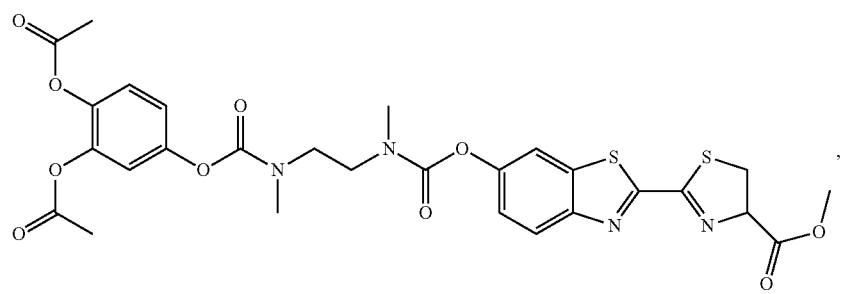
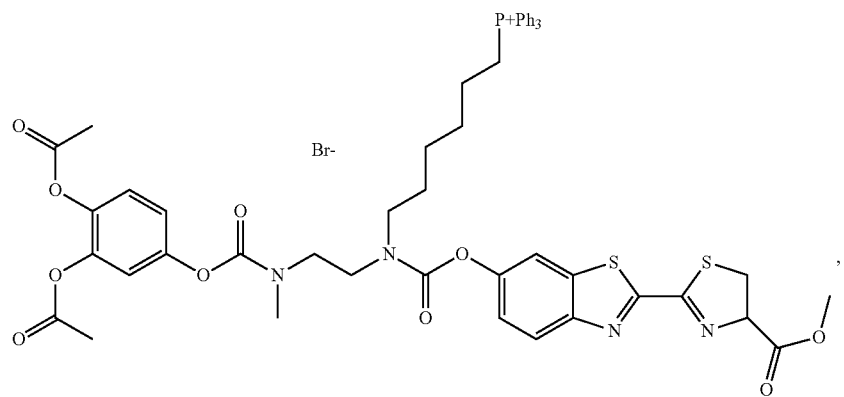
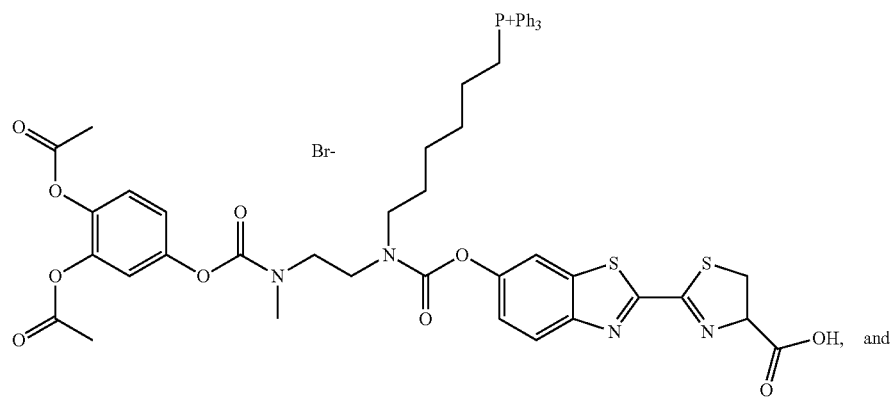

-continued

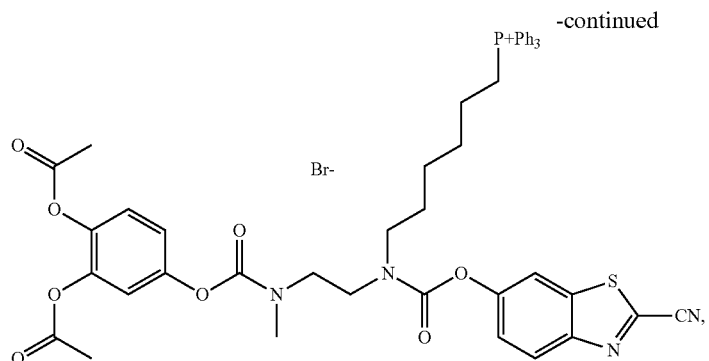

and salts thereof.

In one aspect, the disclosure provides a method of detecting superoxide in a sample, comprising:

contacting the sample with a compound disclosed herein (e.g., a compound of formula (I) or formula (II));

contacting the sample with a luciferin-utilizing luciferase, if it is not already present in the sample; and detecting luminescence in the sample.

In some embodiments, the sample comprises live cells. In some embodiments, the cells express the luciferin-utilizing luciferase. In some embodiments, the method comprises adding the luciferin-utilizing luciferase to the sample. In some embodiments, the luciferin-utilizing luciferase is a firefly luciferase or a click beetle luciferase.

In one aspect, the disclosure provides a kit comprising a compound a compound disclosed herein (e.g., a compound of formula (I) or formula (II)). In some embodiments, the kit further comprises a luciferin-utilizing luciferase enzyme or a nucleotide sequence encoding a luciferin-utilizing luciferase enzyme. In some embodiments, the kit further comprises a buffer reagent.

Other aspects and embodiments will become apparent in light of the following description and drawings.

BRIEF DESCRIPTION OF THE DRAWINGS

FIGS. 1A-1B show schematic overviews of methods of detecting superoxide in cells using compounds such as those disclosed herein. Unstable superoxide generated outside (FIG. 1A) or inside (FIG. 1B) cells is detected using pro-luciferin probes. Upon superoxide production, pro-luciferin probes rapidly react with highly unstable superoxide to generate stable luciferin product. Luciferin is detected using luciferase reaction with luminescence signal being proportional to superoxide production.

FIGS. 6A-6B show data from assays to detect superoxide production by macrophages as described in Example 5.

DETAILED DESCRIPTION

Figure 2:
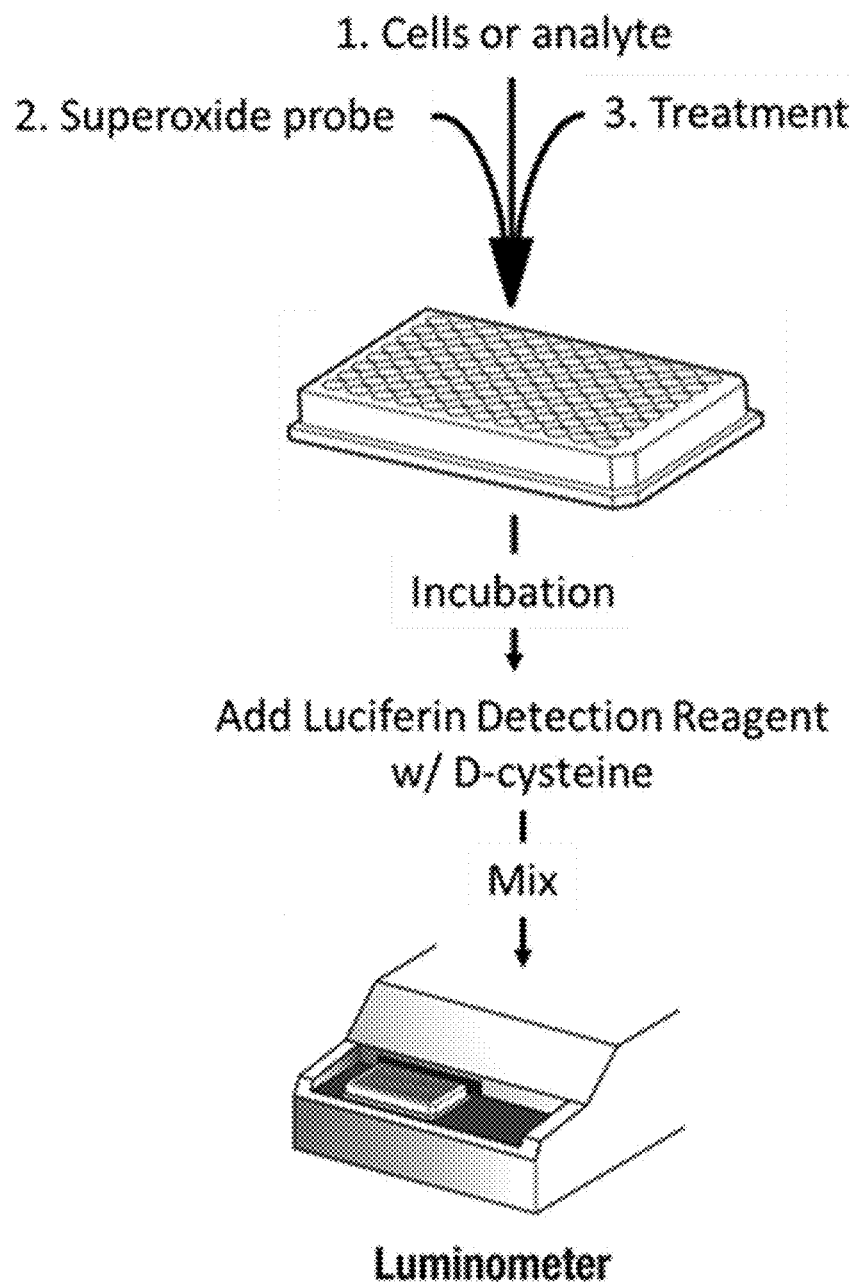
FIG. 2 shows a schematic overview of a luminescence assay to detect superoxide in a sample of cells or other analyte; the "treatment" step refers to addition of an unknown experimental component (e.g., a drug candidate), which can be added before, after, or simultaneously with the superoxide probe.

Disclosed herein are probe compounds, particularly caged luciferin and hydroxycyanobenzothiazole compounds and derivatives thereof, that have high specificity for detection of superoxide over other reactive oxygen species. Upon reaction with superoxide, a stable reporter product is formed, allowing assays to be conducted in an "add and read" plate-based format, or in kinetic mode by media sampling.

Definitions

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies, or protocols as herein described as these may vary in accordance with routine experimentation and optimization. It is also to be understood that the terminology used in the description is for the purpose of describing the particular versions or embodiments only and is not intended to limit the scope of the embodiments described herein.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein and in the appended claims, the singular forms "a", "an", and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc., without the exclusion of the presence of additional feature(s), element(s), method step(s), etc. Conversely, the term "consisting of" and linguistic variations thereof, denotes the presence of recited feature(s), element(s), method step(s), etc., and excludes any unrecited feature(s), element(s), method step(s), etc., except for ordinarily-associated impurities. The phrase "consisting essentially of" denotes the recited feature(s), element(s), method step(s), etc., and any additional feature(s), element(s), method step(s), etc., that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Luminescence" refers to the light output of a luciferase enzyme under appropriate conditions, e.g., in the presence of a suitable substrate such as a luciferin or hydroxycyanobenzothiazole compound (e.g., one that has been generated following reaction of superoxide with a compound of formula (I) or formula (II)). The light output may be measured as an instantaneous or near-instantaneous measure of light output (which is sometimes referred to as "T=0" luminescence or "flash") at the start of the luminescence reaction, which may be initiated upon addition of the luciferin substrate. The reaction chamber (e.g., a plate such as a 96-well plate) may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

As used herein, the term "sample" is used in its broadest sense. In one sense, it is meant to include a specimen or culture obtained from any source as well as biological and environmental samples. Biological samples may be obtained from animals (including humans) and encompass fluids, solids, tissues, and gases. Biological samples include blood products such as plasma, serum, and the like. Sample may also refer to cells, cell lysates or purified forms of the enzymes, peptides, and/or polypeptides described herein (e.g., a purified protein sample). Cell lysates may include cells that have been lysed with a lysing agent or lysates such as rabbit reticulocyte or wheat germ lysates. Sample may also include in vitro samples and cell-free samples, such as cell-free expression systems. Environmental samples include environmental material such as surface matter, soil, water, crystals, and industrial samples. Sample may also include purified samples, such as purified protein samples. Such examples are not however to be construed as limiting the sample types applicable to the present invention.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "acyl" refers to a group—C(=O)R, where R is selected from the group consisting of alkyl, alkenyl, alkynyl, aryl, arylalkyl, cycloalkyl, cycloalkylalkyl, heteroaryl, heteroarylalkyl, heterocyclyl, and heterocyclylalkyl.

As used herein, the term "alkyl" means a straight or branched saturated hydrocarbon chain. The alkyl chain can include, e.g., from 1 to 30 carbon atoms ($C_1$-$C_{30}$ alkyl), 1 to 24 carbon atoms ($C_1$-$C_{24}$ alkyl), for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkenyl" means a straight or branched hydrocarbon chain containing at least one carbon-carbon double bond. The double bond(s) may be located at any positions with the hydrocarbon chain. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-l-heptenyl, and 3-decenyl.

As used herein, the term "alkynyl" means a straight or branched hydrocarbon chain containing at least one carbon-carbon triple bond. The triple bond(s) may be located at any positions with the hydrocarbon chain. Representative examples of alkynyl include, but are not limited to, ethynyl, propynyl, and butynyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, and tert-butoxy.

As used herein, the term "amino" refers to a group—$NR_xR_y$, wherein $R_x$ and $R_y$ are selected from hydrogen and alkyl (e.g., $C_1$-$C_4$ alkyl).

As used herein, the term "aryl" refers to an aromatic carbocyclic ring system having a single ring (monocyclic) or multiple rings (e.g., bicyclic or tricyclic) including fused ring systems, and zero heteroatoms. As used herein, 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl).

Representative examples of aryl groups include, but are not limited to, phenyl, naphthyl, anthracenyl, and phenanthrenyl.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "heteroaryl" refers to an aromatic group having a single ring (monocyclic) or multiple rings (bicyclic or tricyclic) having one or more ring heteroatoms independently selected from O, N, and S. The aromatic monocyclic rings are five- or six-membered rings containing at least one heteroatom independently selected from O, N, and S (e.g., 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. The heterocycle can be monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. The heteroatom in the ring can be oxidized (e.g., if the ring heteroatom is S, it can be oxidized to SO or $SO_2$). Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan,hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

As used herein, the term "hydroxy" means an —OH group.

As used herein, the term "targeting moiety" refers to a moiety that binds to or localizes to a specific locale. The moiety may be, for example, a small molecule, a peptide, a protein, a nucleic acid, a nucleic acid analog, or a carbohydrate. The locale may be an organelle, a subcellular compartment, a particular cell type, or a particular tissue.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable substituent group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

represents a point of attachment of one moiety to another moiety (e.g., a substituent group to the rest of the compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—, and —OC(O)NH— also optionally recites —NHC(O)O—.

Compounds

Disclosed herein are compounds of formula (II):

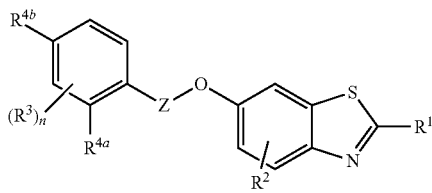

(II)

or a salt thereof, wherein:

R$^1$ is selected from —CN and

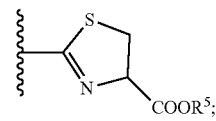

R$^2$ is selected from hydrogen and halo;

n is 0, 1, 2, or 3; and each R$^3$ is independently selected from C$_1$-C$_4$ alkyl, C$_1$-C$_4$ alkoxy, —OC(O)-C$_1$-C$_4$ alkyl, hydroxy, amino, and a group -Linker-X, wherein X is a targeting moiety;

one of R$^{4a}$ and R$^{4b}$ is hydroxy or —OC(O)-C$_1$-C$_4$ alkyl, and the other is hydrogen or a group -Linker-X, wherein X is a targeting moiety;

R$^5$ is selected from hydrogen and C$_1$-C$_4$ alkyl;

Z is a bond or a group of formula

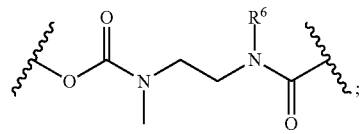

and

R$^6$ is selected from C$_1$-C$_4$ alkyl and a group -Linker-Y, wherein Y is a targeting moiety.

In some embodiments, R$^1$ is —CN. In such embodiments, the compound is a compound of formula (II"):

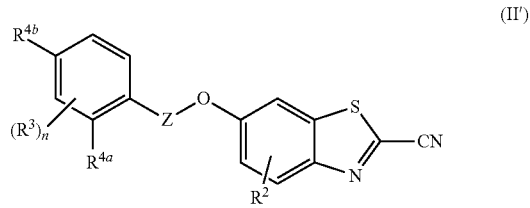

(II')

or a salt thereof, wherein R$^2$, n, R$_3$, R$^{4a}$, R$^{4b}$, and Z are as defined and described herein.

In some embodiments, R$^1$ is

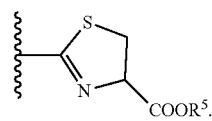

In such embodiments, the compound is a compound of formula (II"):

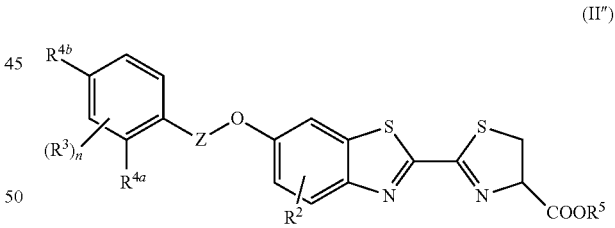

(II")

or a salt thereof, wherein R$^2$, n, R$_3$, R$^{4a}$, R$^{4b}$, R$^5$, and Z are as defined and described herein.

In some embodiments, R$^2$ is hydrogen. In some embodiments, R$^2$ is halo. In some embodiments, R$^2$ is fluoro.

In some embodiments, Z is a bond. In some embodiments, Z is a group of formula

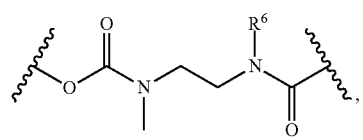

wherein $R^6$ is selected from $C_1$-$C_4$ alkyl and a group -Linker-Y, and Y is a targeting moiety. In some embodiments, Z is a group of formula

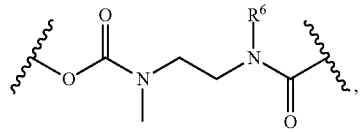

wherein $R^6$ is selected from methyl and a group -Linker-Y, and Y is a targeting moiety. In some embodiments, Z is a group of formula

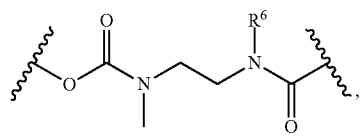

wherein $R^6$ is methyl. In some embodiments, Z is a group of formula

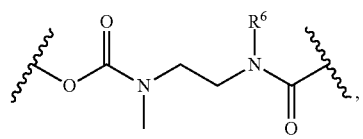

wherein $R^6$ is a group -Linker-Y, and Y is a targeting moiety.

In some embodiments, $R^{4a}$ is hydrogen and $R^{4b}$ is hydroxy or —OC(O)-$C_1$-$C_4$ alkyl. In some embodiments, $R^{4a}$ is hydrogen and $R^{4b}$ is hydroxy. In some embodiments, $R^{4a}$ is hydrogen and $R^{4b}$ is —OC(O)CH$_3$. In some embodiments, $R^{4a}$ is hydroxy and $R^{4b}$ is hydrogen. In some embodiments, $R^{4a}$ is hydroxy and $R^{4b}$ is a group -Linker-X, wherein X is a targeting moiety.

In some embodiments, the group

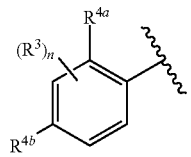

in formula (II) has a formula selected from:

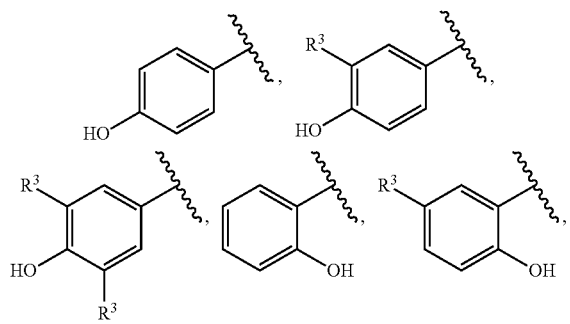

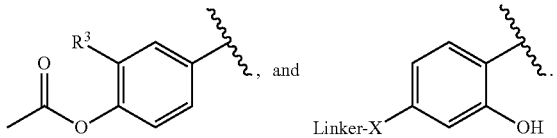

In some embodiments, n is 0, 1, or 2. In some embodiments, n is 0. In some embodiments, n is 1. In some embodiments, n is 2.

In some embodiments, each $R^3$ is independently selected from $C_1$-$C_4$ alkyl, $C_1$-$C_4$ alkoxy, —OC(O)-$C_1$-$C_4$ alkyl, and hydroxy. In some embodiments, each $R^3$ is independently selected from $C_1$-$C_4$ alkyl and $C_1$-$C_4$ alkoxy. In some embodiments, each $R^3$ is independently selected from $C_1$-methyl, methoxy, —OC(O)CH$_3$, and hydroxy. In some embodiments, each $R^3$ is independently selected from methyl and methoxy. In some embodiments, each $R^3$ is independently selected from —OC(O)CH$_3$ and hydroxy. In some embodiments, n is 1, and $R^3$ is methyl. In some embodiments, n is 1, and $R^3$ is methoxy. In some embodiments, n is 1, and $R^3$ is —OC(O)CH$_3$. In some embodiments, n is 1, and $R^3$ is hydroxy.

In some embodiments, $R^5$ is hydrogen. In some embodiments, $R^5$ is $C_1$-$C_4$ alkyl (e.g., methyl).

Also disclosed herein are compounds of formula (I):

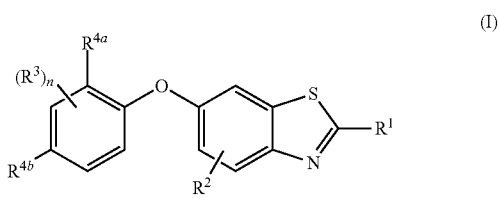

(I)

or a salt thereof, wherein:
$R^1$ is selected from —CN and

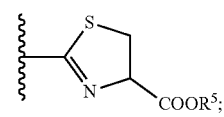

$R^2$ is selected from hydrogen and halo;
n is 0, 1, 2, or 3; and
each $R^3$ is independently selected from $C_1$-$C_4$ alkyl, $C_1$-$C_4$ alkoxy, amino, and a group -Linker-X, wherein X is a targeting moiety;
one of $R^{4a}$ and $R^{4b}$ is hydroxy and the other is hydrogen or a group -Linker-X, wherein X is a targeting moiety; and
$R^5$ is selected from hydrogen and $C_1$-$C_4$ alkyl.

In some embodiments, $R^1$ is —CN. In such embodiments, the compound is a compound of formula (I'):

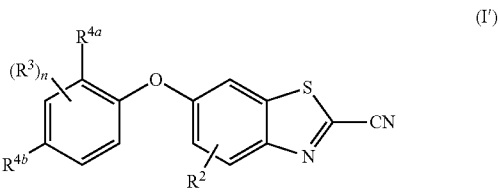

(I')

or a salt thereof, wherein $R^2$, n, $R^3$, $R^{4a}$, and $R^{4b}$ are as defined and described herein.

In some embodiments, $R^1$ is

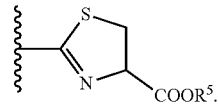

In such embodiments, the compound is a compound of formula (I″):

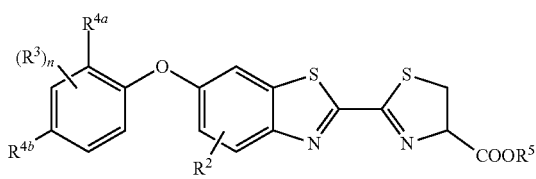

(I″)

or a salt thereof, wherein $R^2$, n, $R^3$, $R^{4a}$, $R^{4b}$, and $R^5$ are as defined and described herein.

In some embodiments, the compound is a compound of formula (Ia):

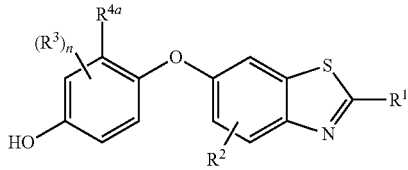

(Ia)

or a salt thereof, wherein $R^1$, $R^2$, n, and $R^3$ are as defined and described herein, and $R^{4a}$ hydrogen or a group -Linker-X, wherein X is a targeting moiety.

In some embodiments, the compound is a compound of formula (Ia′) or (Ia″):

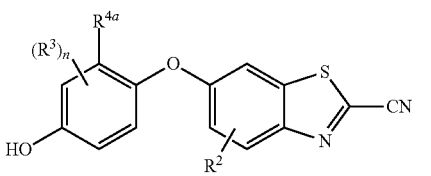

(Ia′)

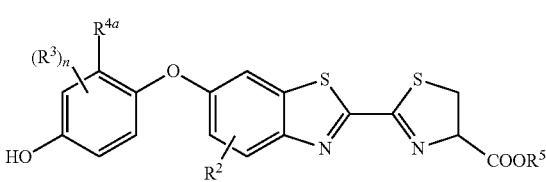

(Ia″)

or a salt thereof, wherein $R^2$, n, and $R^3$ are as defined and described herein, $R^{4a}$ is hydrogen or a group -Linker-X, wherein X is a targeting moiety, and $R^5$ is hydrogen or methyl.

In some embodiments, the compound is a compound of formula (Ib):

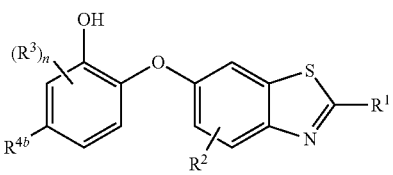

(Ib)

or a salt thereof, wherein $R^1$, $R^2$, n, and $R^3$ are as defined and described herein, and $R^{4b}$ is hydrogen or a group -Linker-X, wherein X is a targeting moiety.

In some embodiments, the compound is a compound of formula (Ib′) or (Ib″):

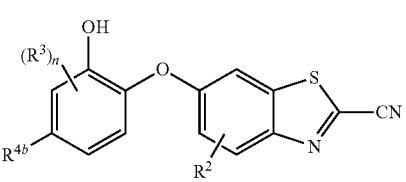

(Ib′)

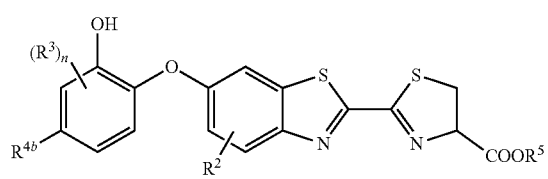

(Ib″)

or a salt thereof, wherein $R^2$, n, and $R^3$ are as defined and described herein, $R^{4b}$ is hydrogen or a group -Linker-X, wherein X is a targeting moiety, and $R^5$ is hydrogen or methyl.

In some embodiments, $R^2$ is hydrogen. In some embodiments, $R^2$ is halo. In some embodiments, $R^2$ is fluoro.

In some embodiments, $R^{4a}$ is hydrogen and $R^{4b}$ is hydroxy. In some embodiments, $R^{4a}$ is hydroxy and $R^{4b}$ is hydrogen. In some embodiments, $R^{4a}$ droxy and $R^{4b}$ is a group -Linker-X, wherein X is a targeting moiety.

In some embodiments, the group

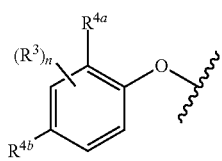

in formula (I) has a formula selected from:

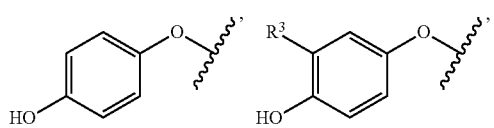

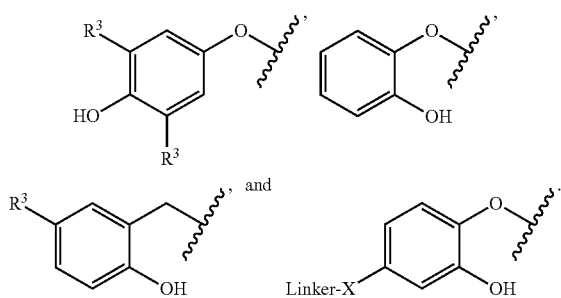

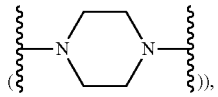

In some embodiments, n is 0, 1, or 2. In some embodiments, n is 0. In some embodiments, n is 1. In some embodiments, n is 2.

In some embodiments, each $R^3$ is independently selected from $C_1$-$C_4$ alkyl and $C_1$-$C_4$ alkoxy. In some embodiments, each $R^3$ is independently selected from methyl and methoxy.

In some embodiments, $R^5$ is hydrogen. In some embodiments, $R^5$ is $C_1$-$C_4$ alkyl (e.g., methyl).

In some embodiments, the compounds include at least one group that is a targeting moiety. In some embodiments, at least one $R^3$, or one of $R^{4a}$ and $R^{4b}$, is a group -Linker-X, wherein X is a mitochondrial targeting moiety. In some embodiments, $R^6$ is a group -Linker-Y, in which Y is a mitochondrial targeting moiety. In such embodiments, the compound can be targeted to a particular locale, such as a particular organelle such as a mitochondrion. Mitochondrial targeting may be particularly useful for the compounds disclosed herein, as mitochondria produce superoxide when electrons that "leak" from the electron transfer system are captured by molecular oxygen. Specific targeting of a selective superoxide probe to the mitochondria can allow for direct measurement of superoxide generated in the mitochondria, e.g., in live cells. For example, in some embodiments, at least one $R^3$, or one of $R^{4a}$ and $R^{4b}$, is a group -Linker-X, wherein X is a triphenylphosphonium moiety or a trialkylammonium moiety. In some embodiments, at least one $R^3$, or one of $R^{4a}$ and $R^{4b}$, is a group -Linker-X, wherein X is a triphenylphosphonium moiety. In some embodiments, $R^6$ is a group -Linker-Y, wherein Y is a triphenylphosphonium moiety or a trialkylammonium moiety. In some embodiments, $R^6$ is a group -Linker-Y, wherein Y is a triphenylphosphonium moiety.

The Linker can be any group that provides sufficient distance between the targeting moiety X or Y and the rest of the compound, to allow each to function undisturbed (or minimally disturbed) by the linkage to the other. The Linker can include one or more groups independently selected from methylene (—CH$_2$—), ether (—O—), amine (—NH—), alkylamine (—NR—, wherein R is an optionally substituted $C_1$-$C_6$ alkyl group), thioether (—S—), disulfide (—S—S—), amide (—C(O)NH—), ester (—C(O)O—), carbamate (—OC(O)NH—), sulfonamide (—S(O)$_2$NH—), arylene (e.g., phenylene (—C$_6$H$_4$—)), heterocyclylene (e.g., piperazinylene and any combination thereof. In some embodiments, the Linker comprises one or more —(CH$_2$CH$_2$O)— (oxyethylene) groups In some embodiments, the Linker comprises one or more alkylene groups (e.g., —(CH$_2$)$_n$—, wherein n is 1-12, e.g., 1, 2, 3, 4, 5, 6, 7, 8, 9, 10, 11, or 12, or any suitable range therebetween). In some embodiments, the Linker comprises one or more branched alkylene groups. In some embodiments, the Linker comprises at least one amide group (—C(O)NH—). In some embodiments, the Linker comprises one or more substituents, pendants, side chains, etc., comprising any suitable organic functional groups (e.g., —OH, —NH$_2$, —SH, —CN, =O, =S, halogen (e.g., —F, —Cl, —Br, —I), —COOH, —CONH$_2$, —CH$_3$, etc.). In some embodiments, the Linker comprises more than one linearly connected C, S, N, and/or O atoms. In some embodiments, the Linker comprises 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therebetween (e.g., 2-20, 10-50, 6-18)). In some embodiments, the Linker comprises 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)).

In some embodiments, the Linker is a straight-chain alkylene linker, e.g., the Linker has a formula —(CH$_2$)$_n$—, wherein n is 1, 2, 3, 4, 5, 6, 7, 8, 9, 10, 11, or 12. In some embodiments, n is 4, 5, 6, 7, or 8. In some embodiments, n is 6, i.e., the Linker has a formula:

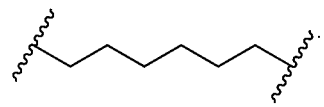 [SMILES: *CCCCCC*]

In some embodiments, the Linker comprises a combination of methylene (—CH$_2$—), ether (—O—), and amide (—C(O)NH—) moieties. For example, in some embodiments, the linker has a formula:

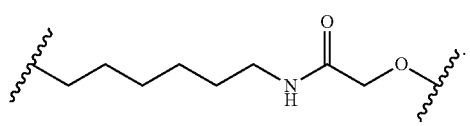 [SMILES: *CCCCCCNC(=O)CO*]

In some embodiments, the compound is selected from the group consisting of:

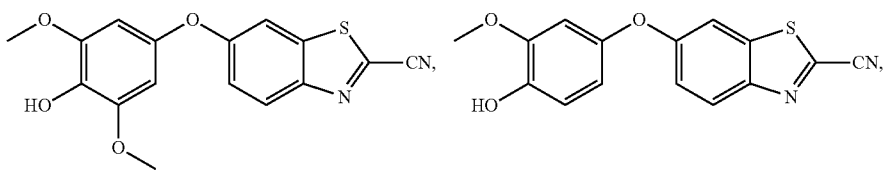

-continued
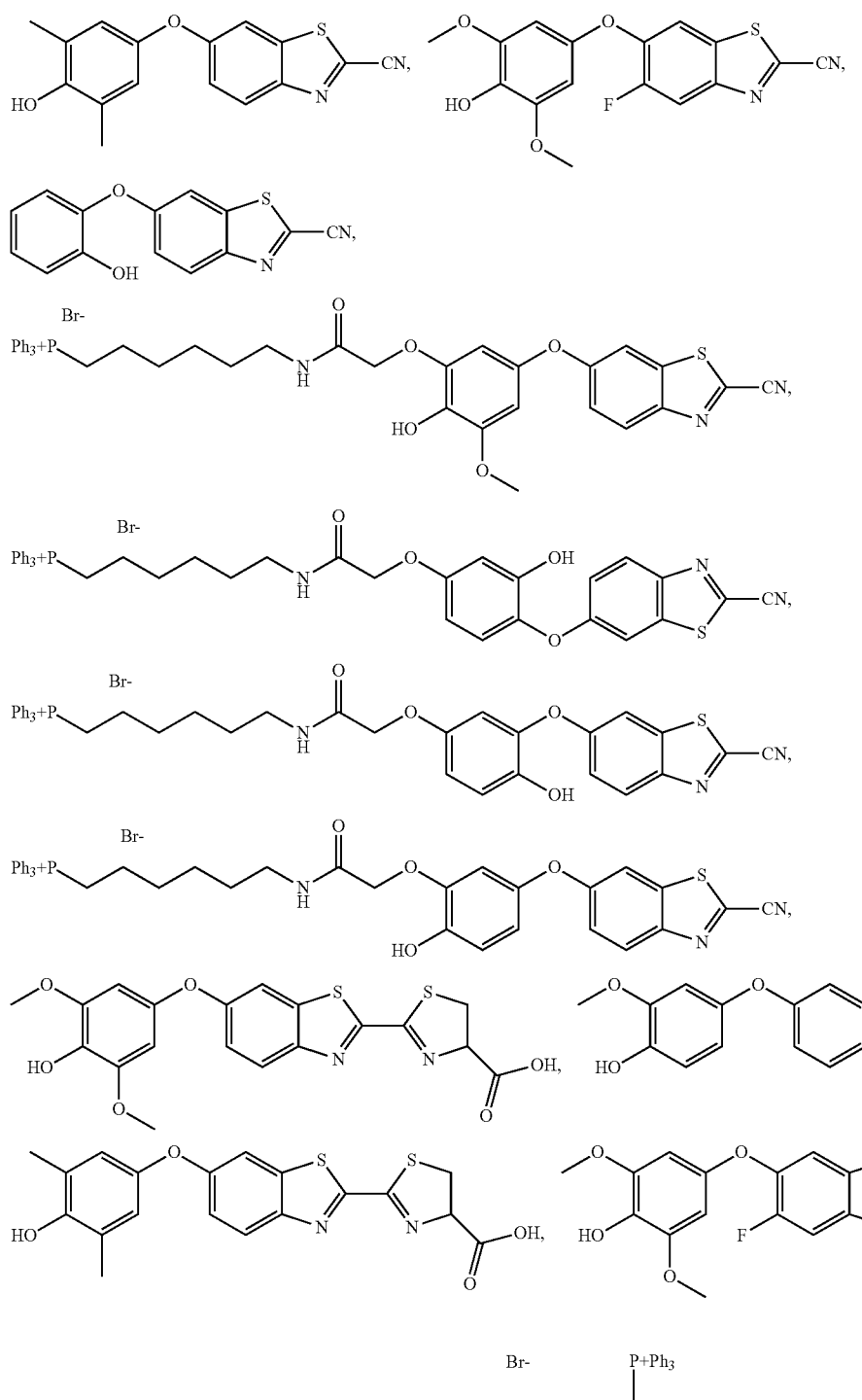
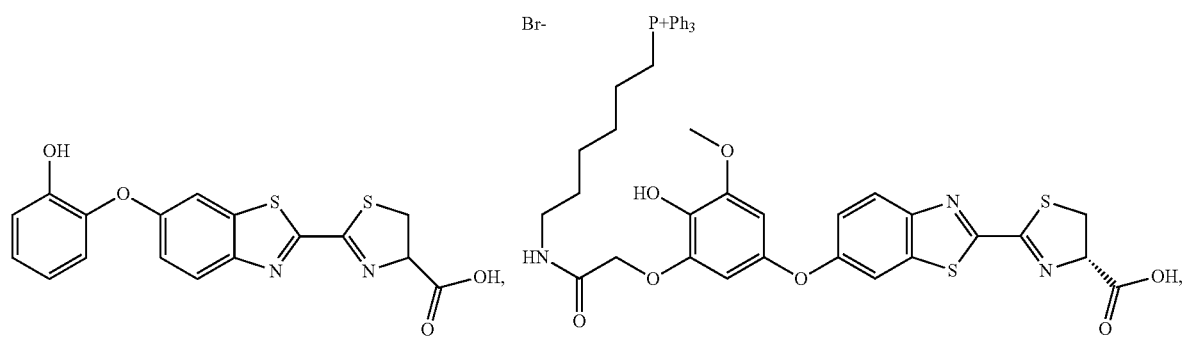

-continued
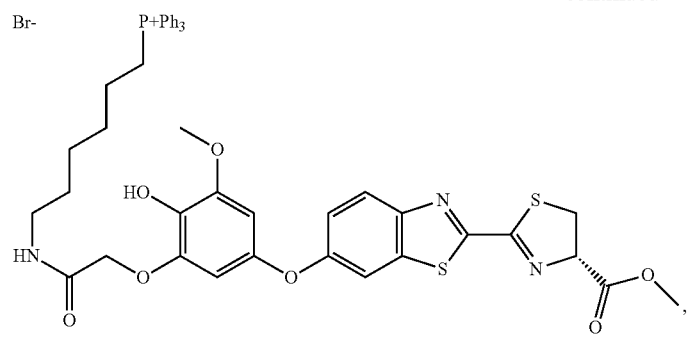
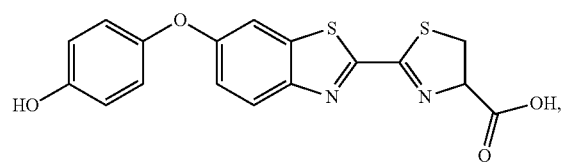
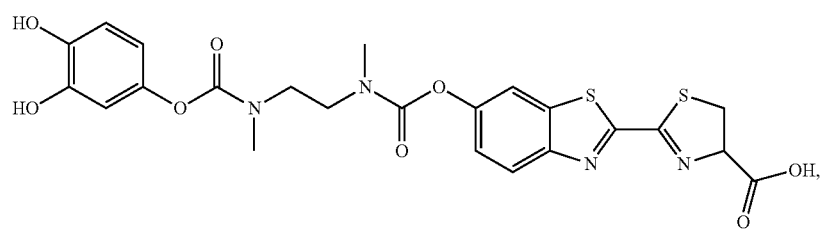
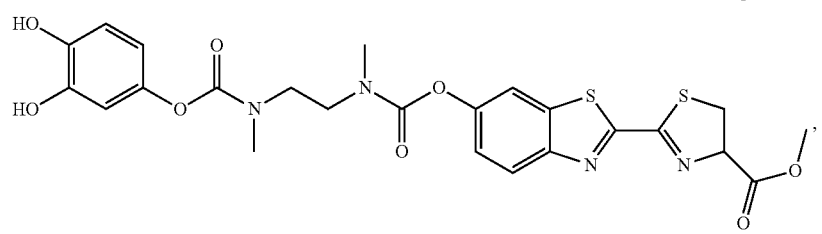
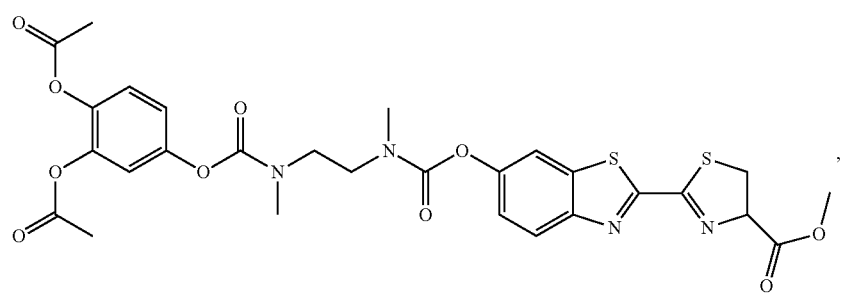
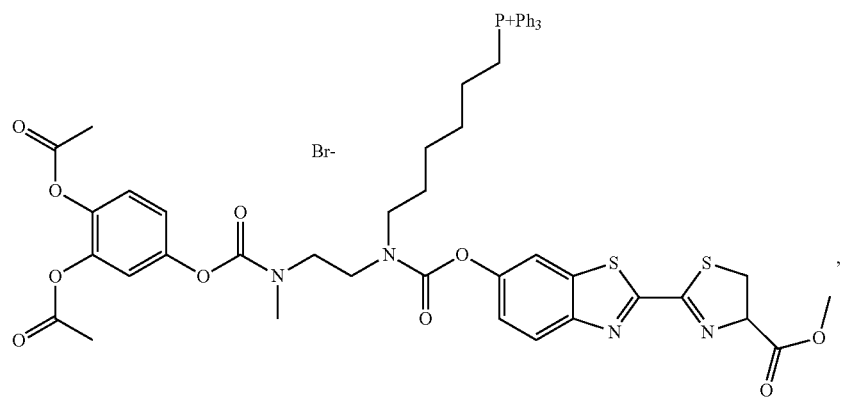

-continued

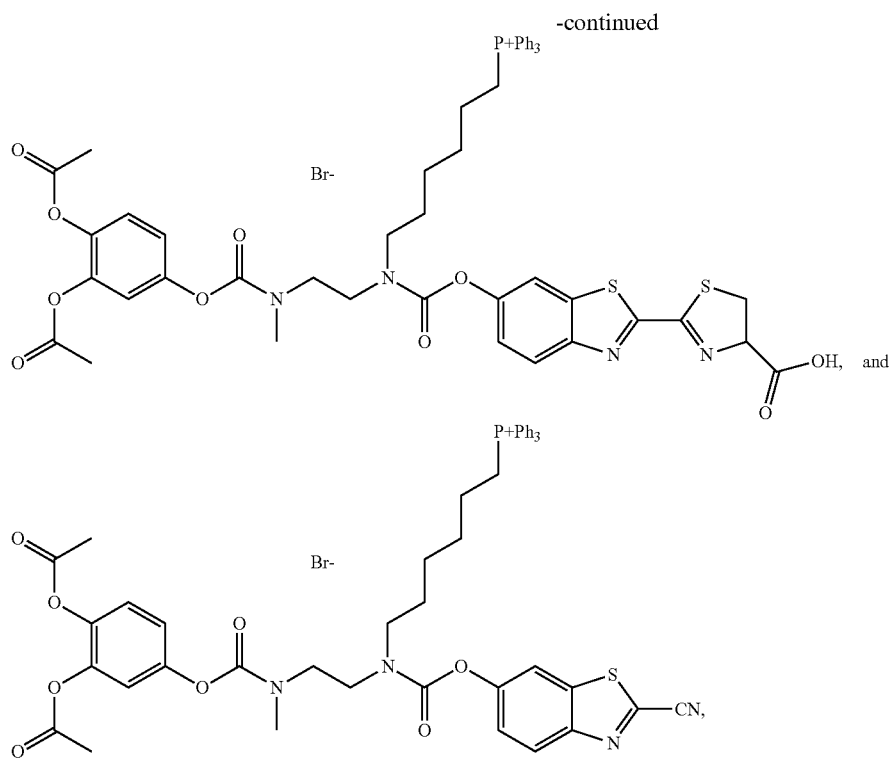

and salts thereof.

In some embodiments, the compound is in a salt form, i.e., a charged form of the parent compound associated with a counterion. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In particular, if a compound is anionic or has a functional group that may be anionic (e.g., —COOH may be —COO$^-$), then a salt may be formed with one or more suitable cations. Examples of suitable inorganic cations include, but are not limited to, alkali metal cations such as Li$^+$, Na$^+$, and K$^+$, alkaline earth cations such as Ca$^{2+}$ and Mg$^{2+}$, and other cations. Potassium and sodium salts may be particularly suitable. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, and NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids such as lysine and arginine. In some embodiments, the compound is a potassium salt. In some embodiments, the compound is a sodium salt.

If a compound cationic or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, tetrafluoroboric, toluenesulfonic, trifluoromethanesulfonic, and valeric. In some embodiments, the compound is a halide salt, such as a chloride, bromide, or iodide salt. In some embodiments, the compound is a tetrafluoroborate or trifluoromethanesulfonate salt.

The compounds can be prepared by a number of suitable methods, some of which are shown in the Examples. Compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization, or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the disclosure or the claims. Alternatives, modifications, and equivalents of the synthetic methods and specific examples are contemplated.

The present disclosure also includes isotopically-labeled compounds, which are identical to those recited in formula (I) and formula (II), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Isotopically-labeled compounds of formula (I) and formula (II) can generally be prepared by conventional techniques known to those skilled in the art or by processes analogous to those described in the accompanying Examples using appropriate isotopically-labeled reagent in place of non-isotopically-labeled reagent.

Methods of Use, Systems, and Kits

Disclosed herein are methods of detecting superoxide using the compounds disclosed herein (e.g., compounds of formula (I) and formula (II), including compounds of formula (I'), (I"), (Ia), (Ia'), (Ia"), (Ib), (Ib'), (Ib"), (II'), and (II")). The compounds feature a moiety, in particular:

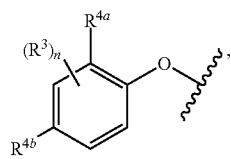

which has an ortho- or para-hydroxy group. This group reacts with superoxide to produce the corresponding quinone compound and release the uncaged luciferin or hydroxycyanobenzothiazole compound, the latter of which is a substrate for a luciferin-utilizing luciferase enzyme, which produces luminescence. Luciferases that utilize luciferin and hydroxycyanobenzothiazole compounds to produce luminescence ("luciferin-utilizing luciferase" or "luciferin-utilizing luciferase enzyme") include those found in various organisms such as beetles (e.g., *Photinus pyralis* and *Photuris pennsylvanica* (fireflies of North America), *Pyrophorus plagiophthalamus* (the Jamaican click beetle)), *Renilla reniformis* (the sea pansy), and several bacteria (e.g., *Xenorhabdus luminescens* and *Vibrio* spp).

Prior to uncaging by reaction with superoxide, compounds of formula (I) and formula (II) are unreactive with the luciferase enzyme, such that luminescence is only observed in the presence of superoxide. The fact that the reactivity arises from superoxide has been confirmed in experiments in which superoxide dismutase is added, which abolishes the signal. As demonstrated in the Examples, the probe compounds disclosed herein have excellent selectivity over other reactive oxygen species such as hydrogen peroxide and singlet oxygen as well as nitrogen species such as sodium nitrite and NONOates.

Without wishing to be bound by theory, the compounds may react with superoxide in a similar manner to hydroquinone, wherein deprotonation followed by single electron oxidation leads to formation of a semiquinone intermediate, which undergoes further oxidation and hydrolysis to release the uncaged luciferin or hydroxycyanobenzothiazole compound and a quinone-type byproduct. Such a reaction for a compound of formula (I) in which $R^1$ is —CN, $R^{4a}$ is hydrogen and $R^{4b}$ is hydroxy is shown in Scheme 1. In some embodiments, compounds of formula (II) can include a biscarbamate linker (i.e., when Z is a group of formula

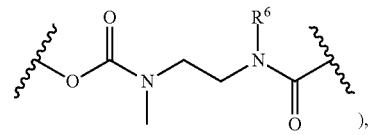

and in such embodiments, deprotonation followed by single electron oxidation leads to the formation of a semiquinone intermediate, which ultimately undergoes further oxidation and hydrolysis, leading to self-immolation of the bis-carbamate linker to release the uncaged luciferin or hydroxycyanobenzothiazole and a quinone-type byproduct from the reactive moiety. Such a reaction for a compound of formula (II) in which $R^1$ is

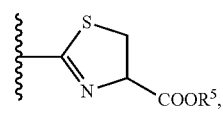

$R^{4a}$ is hydrogen, n is 1, $R^3$ is hydroxy, and $R^{4b}$ is hydroxy is shown in Scheme 2.

Scheme 1.

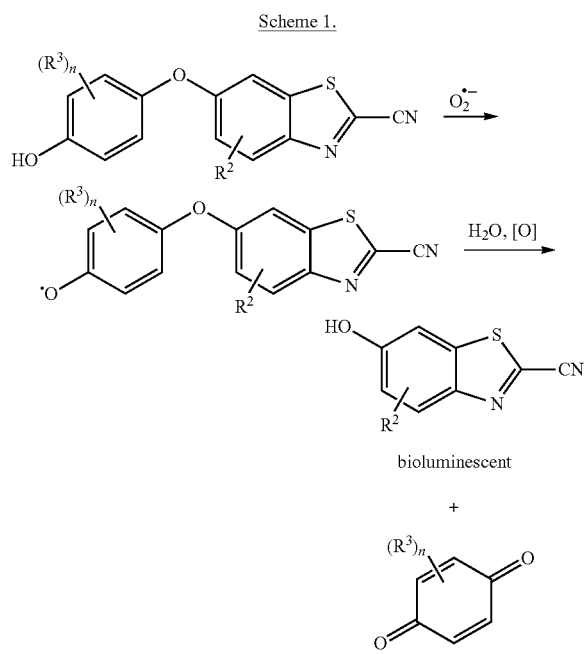

bioluminescent

Scheme 2.

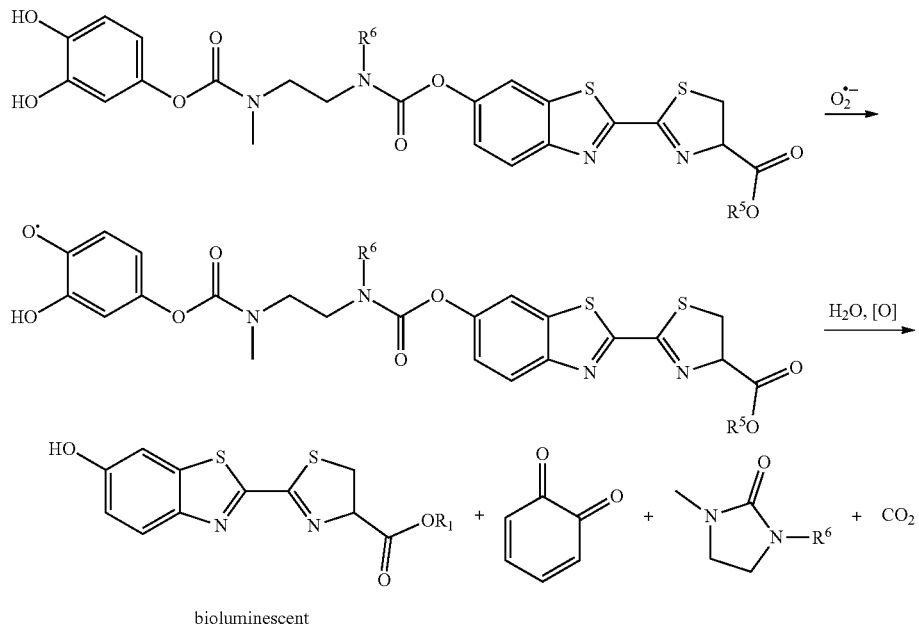

bioluminescent

An advantage of compounds of formula (I) and formula (II) is that the uncaged products are detected by bioluminescence, and no external light is needed (as with fluorescent probes). Furthermore, although superoxide species are highly unstable, upon reaction of the compounds with superoxide, the uncaged compounds are stable. As superoxide species continue to be produced by the cells, the stable uncaged compounds will continue to accumulate and can be detected by measuring the light production (e.g., using the luciferase reaction). Light production will directly correlate with the production of superoxide species and will offer a convenient and quantitative approach for detection of the short-lived superoxide species. The uncaged luciferin or hydroxycyanobenzothiazole compounds can be measured by adding the detection reagent directly to the sample using a homogenous "add and read" format, or by measuring release of luciferin derivatives into the media at different time points by media sampling and luciferin detection.

Accordingly, the present disclosure provides a method for detecting superoxide in a sample, the method comprising: contacting the sample with a compound of formula (I) or formula (II); contacting the sample with a luciferin-utilizing luciferase, if it is not already present in the sample; and detecting luminescence in the sample.

The methods comprise a step of contacting the sample with a compound of formula (I) or formula (II). The compound of formula (I) or formula (II) can be part of a solution that can include other components, such as a solvent, a buffer, a salt, a detergent, an additive, or the like. For example, the compound of formula (I) or formula (II) can be prepared as a solution in a solvent such as dimethylsulfoxide, or as a solution in a buffer such as phosphate-buffered saline. In some embodiments, the method comprises first contacting the sample with a compound of formula (I) or formula (II) and incubating the sample for a period of time, to allow superoxide to react with the compound of formula (I) or formula (II). In some embodiments, this incubation step can be conducted for a period of time of about 1 minute to about 4 days, about 15 minutes to about 1 day, about 1 hour to about 12 hours, or any range therebetween. For example, in some embodiments, the incubation step can be conducted for about 1 hour, about 2 hours, about 3 hours, about 4 hours, about 5 hours, about 6 hours, about 7 hours, about 8 hours, about 9 hours, about 10 hours, about 11 hours, or about 12 hours.

In particular embodiments, a luciferin-utilizing luciferase is not already present in the sample, and accordingly the method comprises a step of contacting the sample with the luciferin-utilizing luciferase. In some embodiments, the luciferin-utilizing luciferase is a firefly luciferase or a click beetle luciferase.

When the luciferin-utilizing luciferase is contacted with the sample, it may be included as part of a luciferase reaction mixture. A "luciferase reaction mixture" contains a luciferin-utilizing luciferase enzyme and other materials that will allow the luciferase enzyme to generate a light signal. The materials needed, and the particular concentrations and/or amounts, of the materials needed to generate a luminescent signal will vary depending on the luciferase enzyme being used. In general, for beetle luciferases, the additional materials can include ATP and a magnesium ($Mg^{2+}$) salt such as magnesium sulfate. In some embodiments, other materials can be added to the solution including: a buffer to maintain the reaction at the proper pH, an additive such as PRIONEX or Bovine serum albumin (BSA) to help maintain luciferase activity, reducing agents, detergents, esterases, salts, amino acids (e.g., D-cysteine), etc. An exemplary luciferase reaction mixture would contain a beetle luciferase, $MgSO_4$, ATP, Tergitol NP-9, and Tricine.

In other embodiments, a luciferin-utilizing luciferase is already present in the sample. For example, in such embodiments, the sample may comprise cells that express a luciferin-utilizing luciferase enzyme.

In some embodiments of the above methods, the method further comprises a step of contacting the sample with another compound, such as a candidate drug compound or any compound for which it would be useful to determine the amount of superoxide produced when the compound is contacted with a sample. In such embodiments, the compound can be contacted with the sample at the same time as the compound of formula (I) or formula (II), or can be added to the sample after the compound of formula (I) or formula (II) has been added.

In an embodiment of a cell-based assay, the cells may be lysed in an appropriate lysis buffer. For animal cells, a buffer with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation, or combinations of these methods may be used. The method of lysis that produces a lysate is compatible with luciferase or other enzyme activity, or the detection of other molecules or conditions.

In any of the above embodiments, the sample may be contained within any suitable vessel. For example, the sample may be in a vial, or in a well of a plate (e.g., a 96-well plate).

In some embodiments, rather than detecting luminescence directly in a well of a plate (e.g., a 96-well plate) using a plate reader, luciferin release into the media can be monitored by removing small amounts of media from the sample and detecting luminescence in the removed media. Such a method can allow for kinetic information on superoxide generation.

The present disclosure further provides a system or kit comprising a compound described herein (i.e., a compound of formula (I) or a salt thereof, or a compound of formula (II) or a salt thereof). The system or kit includes the compound, either alone or in a solvent such as water, DMSO, or a buffer. When the compound is provided alone, the system or kit may further include the solvent in which the compound can be dissolved. The system or kit may further comprise one or more reagents used to carry out an assay to detect superoxide in a sample, e.g., a reagent described above. In some embodiments, the kit further a luciferin-utilizing luciferase enzyme or a nucleotide sequence encoding a luciferin-utilizing luciferase enzyme, such as one described herein.

The system or kit may further include at least one of a container and instructions. For example, the components of the system or kit can be supplied in containers of any sort. For example, sealed glass ampules may contain lyophilized luciferase or buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules. Other containers include test tubes, vials, flasks, bottles, syringes, or the like. Containers may have a sterile access port such as a bottle having a stopper that can be pierced by a hypodermic injection needle. Other containers may have two compartments that are separated by a readily removable membrane that upon removal permits the components to mix. Removable membranes may be glass, plastic, rubber, etc.

The kits may also be supplied with instructional materials. Instructions may be printed on paper or other substrate and/or may be supplied as an electronic-readable medium such as a floppy disc, CD-ROM, DVD-ROM, Zip disc, videotape, audio tape, etc. Detailed instructions may not be physically associated with the kit; instead, a user may be directed to an internet web site, or the instructions may be supplied as electronic mail.

The following examples further illustrate aspects of the disclosure but, of course, should not be construed as in any way limiting its scope.

EXAMPLES

The following abbreviations are used in the Examples: AcOH is acetic acid; DCM is dichloromethane; DIPEA is N,N-diisopropylethylamine; DMA is N,N-dimethylacetamide; DMF is N,N-dimethylformamide; DMSO is dimethylsulfoxide; ES is electrospray; EtOAc is ethyl acetate; h is hours; HATU is 1-[bis(dimethylamino)methylene]-1H-1,2,3-triazolo[4,5-b]pyridinium 3-oxide hexafluorophosphate; HPLC is high performance liquid chromatography; LCMS is liquid chromatography mass spectrometry; MeCN is acetonitrile; MeOH is methanol; RB is round bottom; tBuXPhos-Pd G3 is [(2-di-tert-butylphosphino-2',4',6'-triisopropyl-1,1'-biphenyl)-2-(2'-amino-1,1'-biphenyl)] palladium (II) methanesulfonate; TFA is trifluoroacetic acid; $Tf_2O$ is trifluoromethanesulfonic anhydride; and THF is tetrahydrofuran.

Example 1: Compound Syntheses

Intermediate 1: 2-cyanobenzo [d]thiazol-6-yl trifluoromethanesulfonate

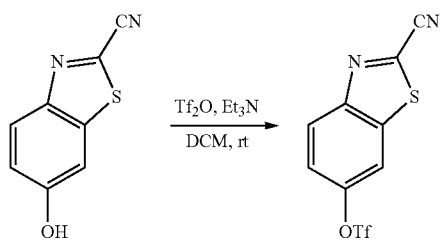 [SMILES: N#Cc1nc2ccc(O)cc2s1 ; N#Cc1nc2ccc(OS(=O)(=O)C(F)(F)F)cc2s1]

To a 250 mL RB flask, 6-hydroxybenzo[d]thiazole-2-carbonitrile (3.00 g, 17.0 mmol) and DCM (80 mL) was added. The mixture was stirred. To the mixture, triethylamine (3.31 mL, (25.5 mmol) followed by drop wise addition of Tf₂O (3.72 mL, 22.1 mmol) was added over 2 minutes. After 10 min, the mixture was concentrated onto Celite and purified by silica gel chromatography with 0-50% EtOAc in heptane as eluent to afford the Intermediate 1: 2-cyanobenzo[d]thiazol-6-yl trifluoromethanesulfonate. LCMS (C₉H₃F₃N₂O₃S₂) (ES, m/z) 309 [M+H]⁺.

Intermediate 2:
2-cyano-5-fluorobenzo[d]thiazol-6-yl trifluoromethanesulfonate

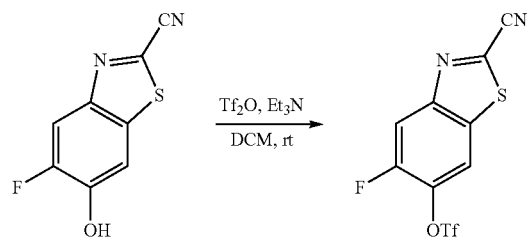 [SMILES: N#Cc1nc2cc(F)c(O)cc2s1 ; N#Cc1nc2cc(F)c(OS(=O)(=O)C(F)(F)F)cc2s1]

Intermediate 2 was prepared in a manner analogous to that of the preparation of Intermediate 1. LCMS (C₉H₂F₄N₂O₃S₂) (ES, m/z) 327 [M+H]⁺.

Intermediate 3: tert-butyl 2-(3,4-dihydroxyphenoxy)acetate

Step 1: tert-butyl 2-(4-formyl-3-hydroxyphenoxy)acetate

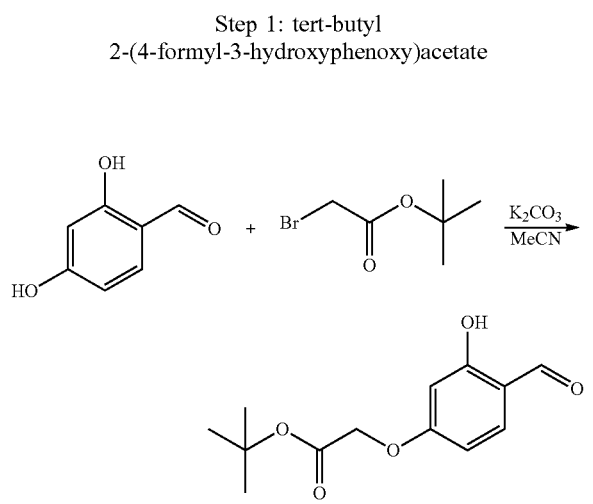

To a 100 mL flask, 2,4-dihydroxybenzaldehyde (1.00 g, 7.24 mmol), K₂CO₃ (1.50 g, 10.9 mmol), and MeCN (15 mL) was added. To the stirring mixture, tert-butyl 2-bromoacetate (1.17 mL, 7.96 mmol) was added. The mixture was stirred and heated at 85° C. for 1 h. The mixture was cooled to room temperature, concentrated onto Celite, and purified by silica gel chromatography with 0-60% EtOAc in heptane as eluent to afford tert-butyl 2-(4-formyl-3-hydroxyphenoxy)acetate. LCMS (C₁₃H₁₆O₅) (ES, m/z) 253 [M+H]⁺.

Step 2: tert-butyl 2-(3,4-dihydroxyphenoxy)acetate

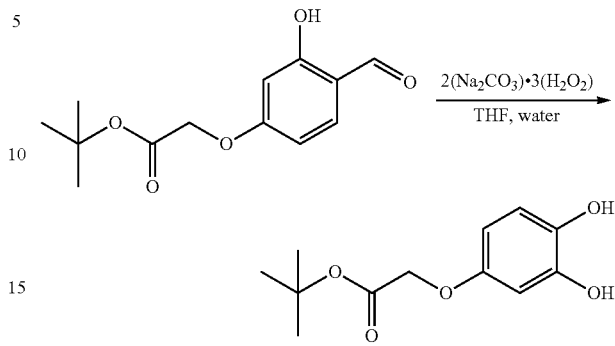

To a 20 mL vial, tert-butyl 2-(4-formyl-3-hydroxyphenoxy)acetate (100 mg, 0.396 mmol), THF (1 mL), and water (1 mL) was added. The solution was stirred and sparged with nitrogen for 1 min. To the vial, sodium percarbonate (124 mg, 0.396 mmol) was added. The mixture was stirred for 30 min. The mixture was quenched with AcOH (0.2 mL). The mixture was extracted with DCM (5 mL). The organic layer was collected with a phase separator. The solvents were evaporated, and the residue was purified by silica gel chromatography with 0-70% EtOAc in heptane as eluent to afford Intermediate 3 (tert-butyl 2-(3,4-dihydroxyphenoxy)acetate). LCMS (C₁₂H₁₆O₅) (ES, m/z) 241 [M+H]⁺.

Intermediate 4: tert-butyl 2-(2,5-dihydroxyphenoxy)acetate

Step 1: tert-butyl 2-(5-formyl-2-hydroxyphenoxy)acetate

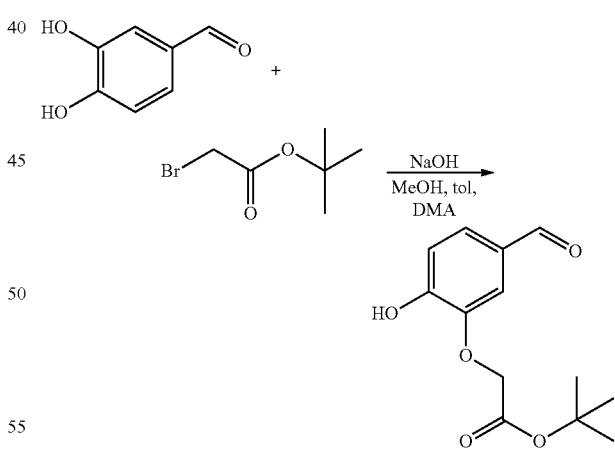

To a 100 mL round bottom flask, 3,4-dihydroxybenzaldehyde (1.00 g, 7.24 mmol), a 4 M solution of NaOH in MeOH (5 mL), and DMA (10 mL) was added. To the stirring mixture, tert-butyl 2-bromoacetate (1.17 mL, 7.96 mmol) as a solution in toluene (5 mL) was added. After 30 seconds, the mixture was quenched with 2 M HCl (~10 mL). The mixture was extracted with diethyl ether (50 mL), and the organic layer was washed with water (3×30 mL). The organic layer was dried over MgSO₄ and filtered, and the solvents were evaporated. The residue was purified by silica gel chromatography with 0-60% EtOAc in heptane to afford tert-butyl 2-(5-formyl-2-hydroxyphenoxy)acetate. LCMS (C$_{13}$H$_{16}$O$_5$) (ES, m/z) 253 [M+H]$^+$.

Step 2: tert-butyl 2-(2,5-dihydroxyphenoxy)acetate

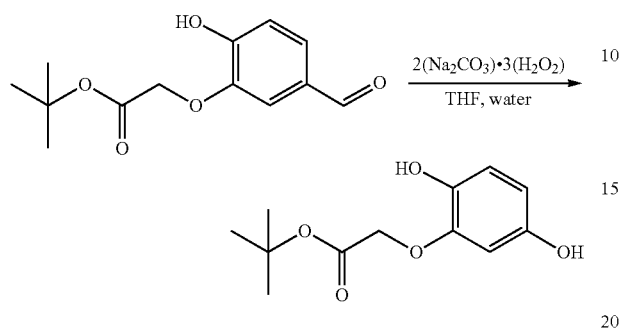

To a 20 mL vial, tert-butyl 2-(5-formyl-2-hydroxyphenoxy)acetate (200 mg, 0.793 mmol), THF (2 mL), and water (2 mL) was added. The solution was stirred and sparged with nitrogen for 1 min. To the vial, sodium percarbonate (249 mg, 0.793 mmol) was added. The mixture was stirred for 2 h under nitrogen. The mixture was quenched with AcOH (0.4 mL). The mixture was extracted with DCM (5 mL). The organic layer was collected with a phase separator. The solvents were evaporated, and the residue was purified by silica gel chromatography with 0-70% EtOAc in heptane as eluent to afford Intermediate 4 (tert-butyl 2-(2,5-dihydroxyphenoxy)acetate). LCMS (C$_{12}$H$_{16}$O$_5$) (ES, m/z) 241 [M+H]$^+$.

Intermediate 5: tert-butyl 2-(2,5-dihydroxy-3-methoxyphenoxy)acetate

Step 1: tert-butyl 2-(5-formyl-2-hydroxy-3-methoxyphenoxy)acetate

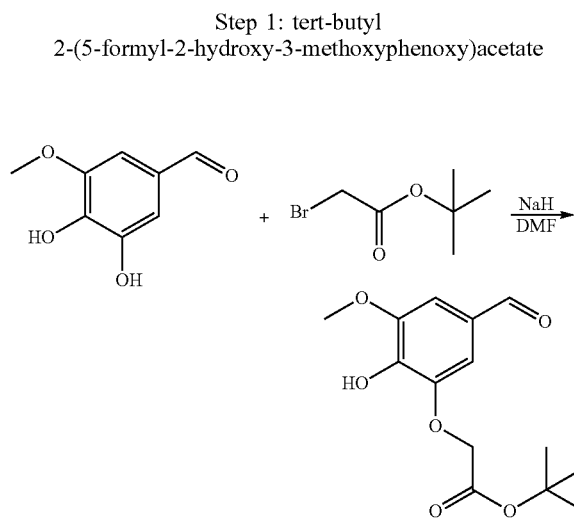

To a 20 mL vial, 3,4-dihydroxy-5-methoxybenzaldehyde (100 mg, 0.595 mmol) and DMF (2.5 mL) was added. The mixture was sparged with nitrogen for 1 min. To the stirring mixture, sodium hydride (60% by weight, 71.4 mg, 1.78 mmol) was added. The mixture was stirred for 15 min. To the mixture, tert-butyl 2-bromoacetate (0.095 mL, 0.654 mmol) was added all at once. After 15 min, the mixture was neutralized with 2 M HCl then diluted with water (5 mL). The mixture was extracted with diethyl ether (20 mL). The organic layer was washed with water (3×20 mL). The organic layer was dried over MgSO$_4$ and filtered, and the solvents were evaporated. The residue was purified by silica gel chromatography with 0-60% EtOAc in heptane to afford tert-butyl 2-(5-formyl-2-hydroxy-3-methoxyphenoxy)acetate. LCMS (C$_{14}$H$_{18}$O$_6$) (ES, m/z) 281 [M+H]$^-$.

Step 2: tert-butyl 2-(2,5-dihydroxy-3-methoxyphenoxy)acetate

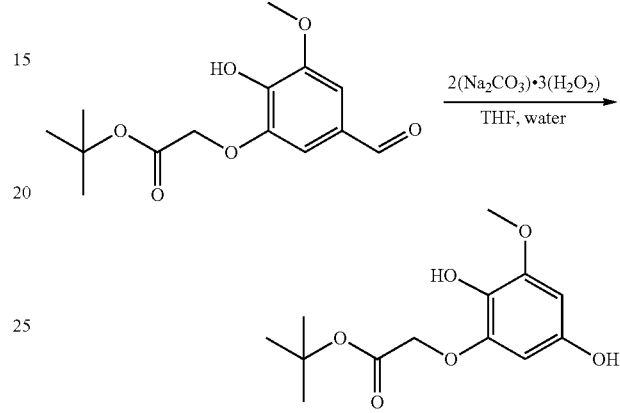

To a 20 mL vial, tert-butyl 2-(5-formyl-2-hydroxy-3-methoxyphenoxy)acetate (80.3 mg, 0.285 mmol), THF (1 mL), and water (1 mL) was added. The solution was stirred and sparged with nitrogen for 1 min. To the vial, sodium percarbonate (89.3 mg, 0.285 mmol) was added. The mixture was stirred for 2 h under nitrogen. The mixture was quenched with AcOH (0.15 mL). The mixture was extracted with diethyl ether. The organic layer was washed with water. The organic layer was dried over MgSO$_4$, and filtered, and the solvents were evaporated. The residue was purified by silica gel chromatography with 0-70% EtOAc in heptane as eluent to afford Intermediate 5 (tert-butyl 2-(2,5-dihydroxy-3-methoxyphenoxy)acetate). LCMS (C$_{13}$H$_{18}$O$_6$) (ES, m/z) 271 [M+H]$^+$.

Intermediate 6: 3,4-bis(benzyloxy)phenol

Step 1: 3,4-bis(benzyloxy)benzaldehyde

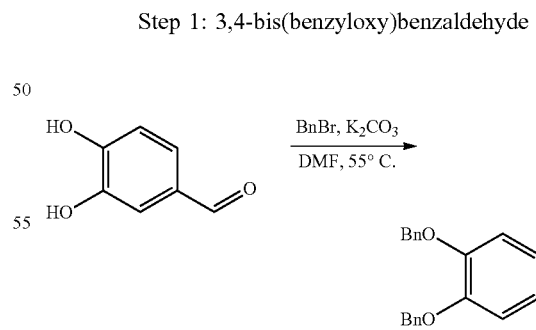

To a 100 mL RB flask, 3,4-dihydroxybenzaldehyde (2.00 g, 14.5 mmol), K$_2$CO$_3$ (6.00 g, 43.4 mmol), DMF (15 mL), and benzyl bromide (4.30 mL, 36.2 mmol) was added. The mixture was stirred and heated at 55° C. for 2 h. The mixture was cooled to room temperature, diluted in EtOAc (70 mL), and filtered through Celite. The solvents were evaporated, and the residue was purified by silica gel chromatography with 0-50% EtOAc in heptane as eluent. The residue from the evaporated fractions was triturated in heptane to afford 3,4-bis(benzyloxy)benzaldehyde. LCMS ($C_{21}H_{18}O_3$) (ES, m/z) 319 [M+H]$^+$.

Step 2: 3,4-bis(benzyloxy)phenol

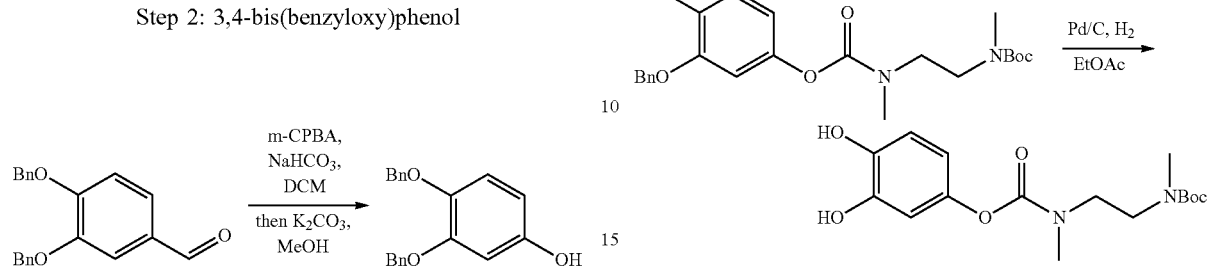

To a 100 mL flask, 3,4-bis(benzyloxy)benzaldehyde (2.00 g, 6.28 mmol), NaHCO$_3$ (1.58 g, 18.9 mmol), m-CPBA (1.63 g, 9.42 mmol), and DCM (20 mL) was added. The mixture was stirred at room temperature for 4 h. The mixture was diluted in DCM (20 mL) and MeOH (20 mL). The mixture was filtered. The filtrate was concentrated. To the residue, K$_2$CO$_3$ (1.73 g, 12.6 mmol) and MeOH (15 mL) was added. The mixture was stirred for 10 min. The mixture was diluted in EtOAc (150 mL) and water (150 mL). The layers were separated, and the organic layer was washed with saturated aqueous K$_2$CO$_3$ (100 mL). The organic layer was dried over sodium sulfate, filtered, and the solvents were evaporated to Intermediate 6 (3,4-bis(benzyloxy)phenol). LCMS ($C_{20}H_{18}O_3$) (ES, m/z) 307 [M+H]$^+$.

Intermediate 7: tert-butyl (3,4-dihydroxyphenyl) ethane-1,2-diylbis(methylcarbamate)

Step 1: 3,4-bis(benzyloxy)phenyl tert-butyl ethane-1,2-diylbis(methylcarbamate)

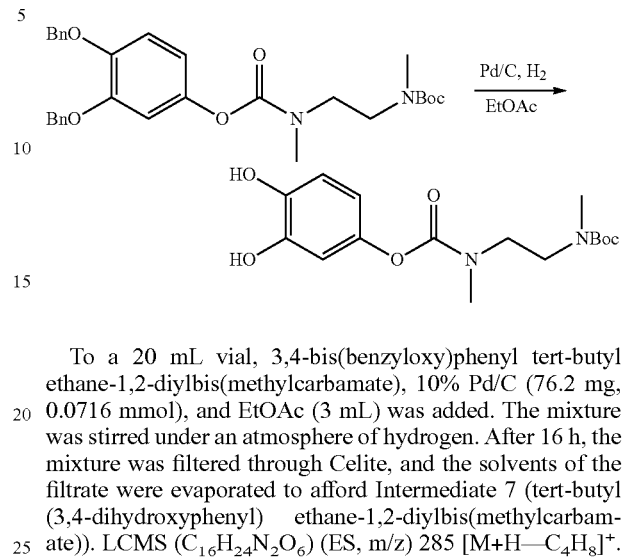

To a 20 mL vial, Intermediate 6 (769 mg, 2.51 mmol), THF (10 mL), and DIPEA (1.75 mL, 10.0 mmol) was added. This mixture was added dropwise to a stirring solution of triphosgene (372 mg, 1.26 mmol) in THF (5 mL) over 1 min. After 5 min, to the mixture was added tert-butyl methyl(2-(methylamino)ethyl)carbamate (0.614 mL, 3.26 mmol). After 20 min, the mixture was adsorbed to Celite and purified by silica gel chromatography with 0-100% EtOAc in heptane as eluent to afford 3,4-bis(benzyloxy)phenyl tert-butyl ethane-1,2-diylbis(methylcarbamate). LCMS ($C_{30}H_{36}N_2O_6$) (ES, m/z) 543 [M+Na]$^+$.

Step 2: tert-butyl (3,4-dihydroxyphenyl) ethane-1,2-diylbis(methylcarbamate)

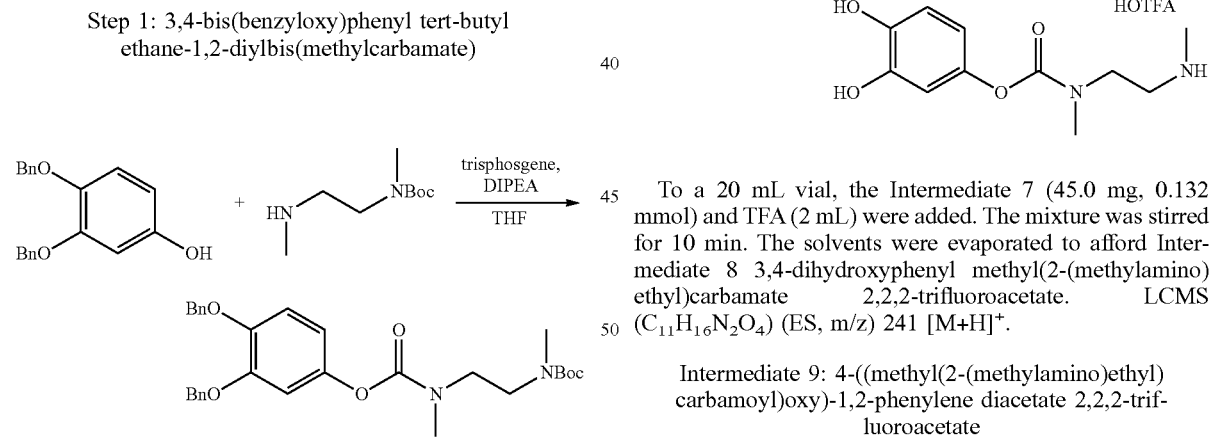

To a 20 mL vial, 3,4-bis(benzyloxy)phenyl tert-butyl ethane-1,2-diylbis(methylcarbamate), 10% Pd/C (76.2 mg, 0.0716 mmol), and EtOAc (3 mL) was added. The mixture was stirred under an atmosphere of hydrogen. After 16 h, the mixture was filtered through Celite, and the solvents of the filtrate were evaporated to afford Intermediate 7 (tert-butyl (3,4-dihydroxyphenyl) ethane-1,2-diylbis(methylcarbamate)). LCMS ($C_{16}H_{24}N_2O_6$) (ES, m/z) 285 [M+H—$C_4H_8$]$^+$.

Intermediate 8: 3,4-dihydroxyphenyl methyl(2-(methylamino)ethyl)carbamate 2,2,2-trifluoroacetate

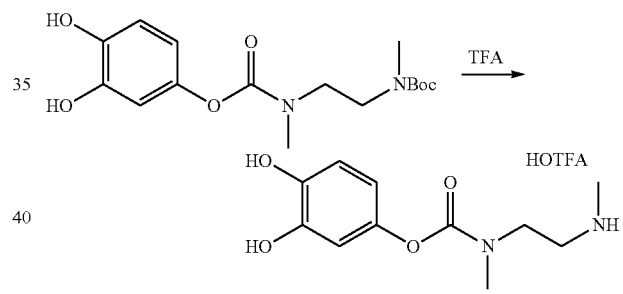

To a 20 mL vial, the Intermediate 7 (45.0 mg, 0.132 mmol) and TFA (2 mL) were added. The mixture was stirred for 10 min. The solvents were evaporated to afford Intermediate 8 3,4-dihydroxyphenyl methyl(2-(methylamino)ethyl)carbamate 2,2,2-trifluoroacetate. LCMS ($C_{11}H_{16}N_2O_4$) (ES, m/z) 241 [M+H]$^+$.

Intermediate 9: 4-((methyl(2-(methylamino)ethyl)carbamoyl)oxy)-1,2-phenylene diacetate 2,2,2-trifluoroacetate

Step 1: 4-(((2-((tert-butoxycarbonyl)(methyl)amino)ethyl)(methyl)carbamoyl)oxy)-1,2-phenylene diacetate

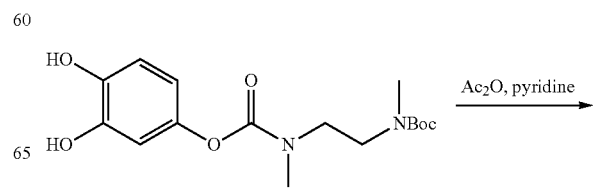

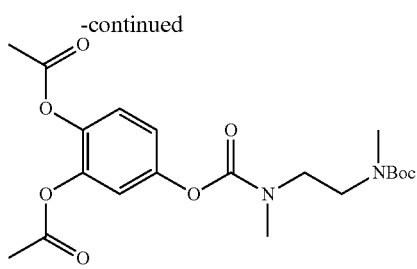

To a 20 mL vial, Intermediate 7 (46.0 mg, 0.135 mmol), acetic anhydride (1 mL), and pyridine (1 mL) was added. The mixture was stirred at room temperature for 10 min. The solvents were evaporated, and the residue was co-evaporated with toluene 3 times to afford 4-(((2-((tert-butoxycarbonyl)(methyl)amino)ethyl)(methyl)carbamoyl)oxy)-1,2-phenylene diacetate. LCMS ($C_{20}H_{28}N_2O_8$) (ES, m/z) 447 [M+Na]$^+$.

Step 2: 4-((methyl(2-(methylamino)ethyl)carbamoyl)oxy)-1,2-phenylene diacetate 2,2,2-trifluoroacetate

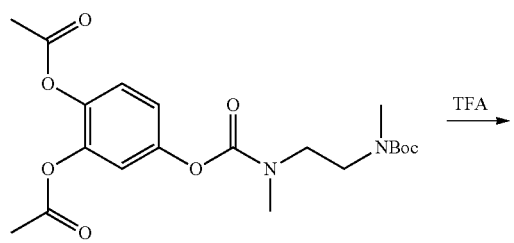

To a 20 mL vial, 4-(((2-((tert-butoxycarbonyl)(methyl)amino)ethyl) -(methyl)carbamoyl)oxy)-1,2-phenylene diacetate (57.0 mg, 0.134 mmol) and TFA (2 mL) was added. The mixture was stirred for 10 min. The solvents were evaporated to afford Intermediate 9 (4-((methyl(2-(methylamino)ethyl)carbamoyl)oxy)-1,2-phenylene diacetate 2,2,2-trifluoroacetate). LCMS ($C_{15}H_{20}N_2O_6$) (ES, m/z) 325 [M+H]$^+$.

Intermediate 10: 2-cyanobenzo[d]thiazol-6-yl (3,4-dihydroxyphenyl) ethane-1,2-diylbis(methylcarbamate)

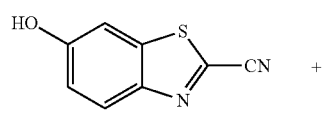

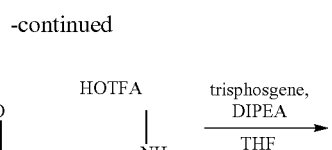

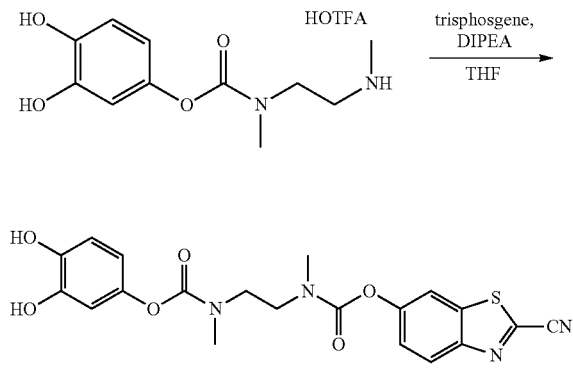

To a 20 mL vial, 6-hydroxybenzo[d]thiazole-2-carbonitrile (19.0 mg, 0.108 mmol), THF (1.5 mL), and DIPEA (0.075 mL, 0.43 mmol) was added. The mixture was added dropwise to a stirring solution of triphosgene (12.8 mg, 0.0431 mmol) in THF (1 mL) over 1 min. After 5 min, to the mixture was added the Intermediate 8 (33.7 mg, 0.140 mmol) in THF (1 mL). After 20 min, the mixture was adsorbed to Celite and purified by silica gel chromatography with 0-100% EtOAc in heptane as eluent to afford Intermediate 10 2-cyanobenzo[d]thiazol-6-yl (3,4-dihydroxyphenyl) ethane-1,2-diylbis(methylcarbamate). LCMS ($C_{20}H_{18}N_4O_6S$) (ES, m/z) 443 [M+H]$^+$.

Intermediate 11: (6-(((3,4-diacetoxyphenoxy)carbonyl)(2-(methylamino)ethyl)amino)hexyl)triphenylphosphonium bromide 2,2,2 trifluoroacetate Step 1: (6-((2-((tert-butoxycarbonyl)(methyl)amino)ethyl)amino)hexyl)triphenylphosphonium bromide

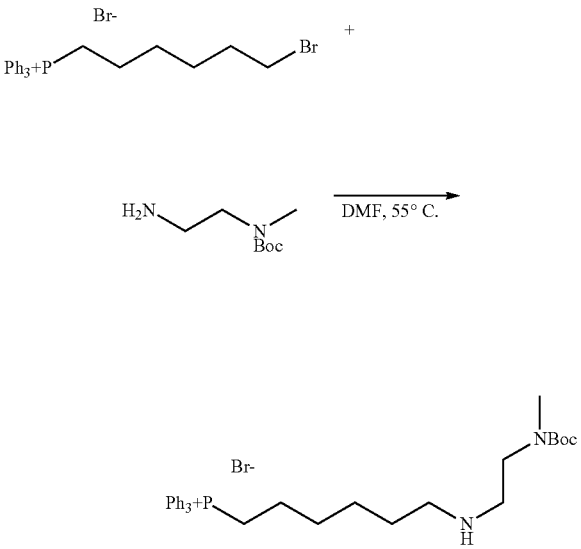

To a 20 mL vial, (6-bromohexyl)triphenylphosphonium bromide (1.00 g, 1.98 mmol) and DMF (10 mL) was added. To this mixture, tert-butyl (2-aminoethyl)(methyl)carbamate (1.72 g, 9.88 mmol) was added. The mixture was stirred and heated at 55° C. for 4 h. The mixture was cooled to room temperature, and the solvents were evaporated. The residue was purified by an amine-functionalized silica gel chromatography with 0-10% MeOH in DCM as eluent. The residue was further purified by triturating with diethyl ether twice, affording (6-((2-((tert-butoxycarbonyl)(methyl)amino)ethyl)amino)hexyl)triphenylphosphonium bromide. LCMS ($C_{32}H_{44}N_2O_2P$) (ES, m/z) 519 $[M]^+$.

Step 2: (6-(((3,4-bis(benzyloxy)phenoxy)carbonyl)(2-((tert-butoxycarbonyl) (methyl)amino)ethyl)amino)hexyl)triphenylphosphonium bromide

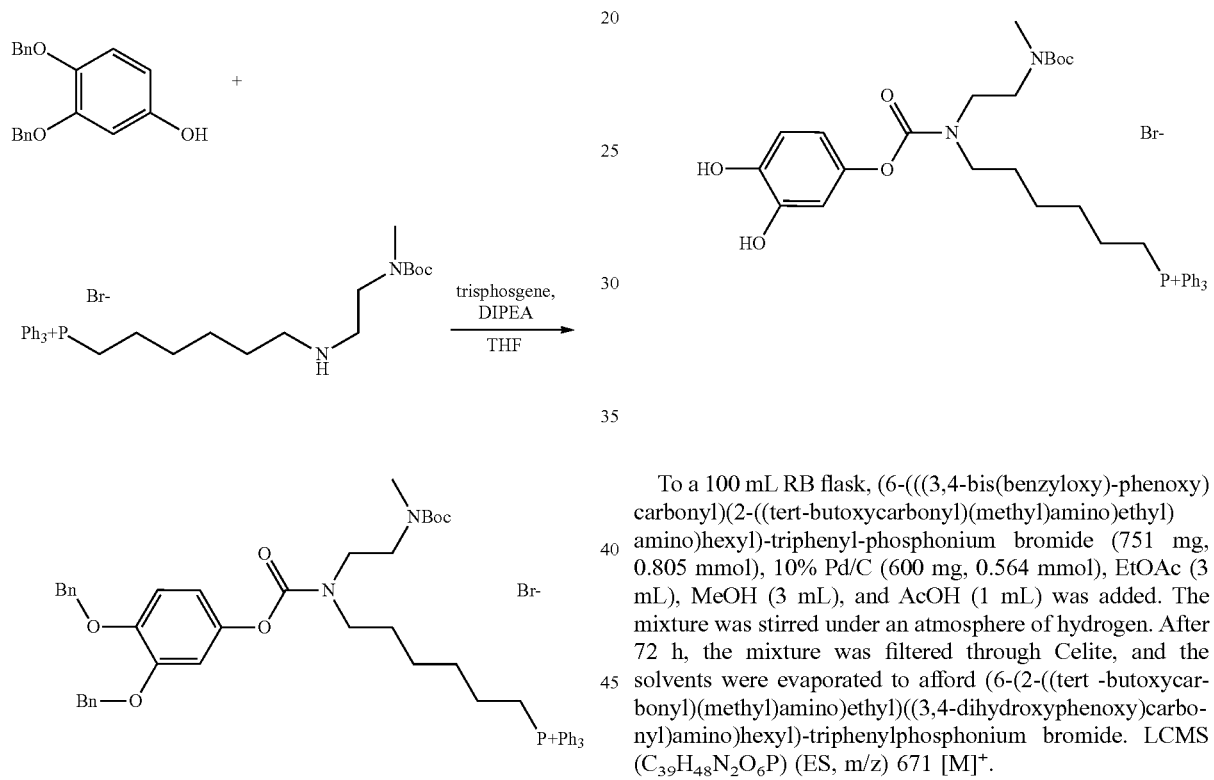

To a 20 mL vial, Intermediate 6 (403 mg, 1.31 mmol), THF (5 mL) and DIPEA (0.931 mL, 5.26 mmol) was added. The mixture was added dropwise to a stirring solution of triphosgene (195 mg, 0.657 mmol) in THF (2 mL) over 1 min. After 15 min, to the mixture was added (6-((2-((tert-butoxycarbonyl)(methyl)amino)ethyl)amino)hexyl)triphenylphosphonium bromide (788 mg, 1.31 mmol) in THF (2 mL). After 20 min, the mixture was adsorbed to Celite and purified by silica gel chromatography with 0-10% MeOH in DCM as eluent. The residue was dissolved in THF (20 mL). Residual DIPEA-HCl salts were precipitated and removed by filtration and washed with THF. The solvents of the filtrate were evaporated to afford (6-(((3,4-bis(benzyloxy)-phenoxy)carbonyl)(2-((tert-butoxycarbonyl)(methyl)amino)ethyl)amino)hexyl) -triphenyl-phosphonium bromide. LCMS ($C_{53}H_{60}N_2O_6P$) (ES, m/z) 851 $[M]^+$.

Step 3: (6-((2-((tert-butoxycarbonyl)(methyl)amino)ethyl)((3,4-dihydroxyphenoxy)carbonyl)amino)hexyl)triphenylphosphonium bromide

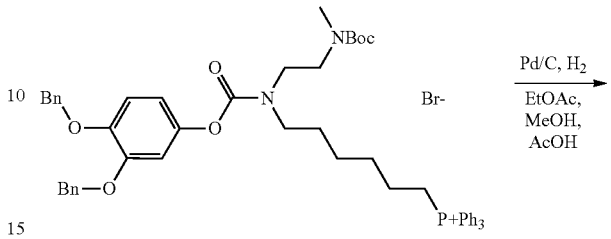

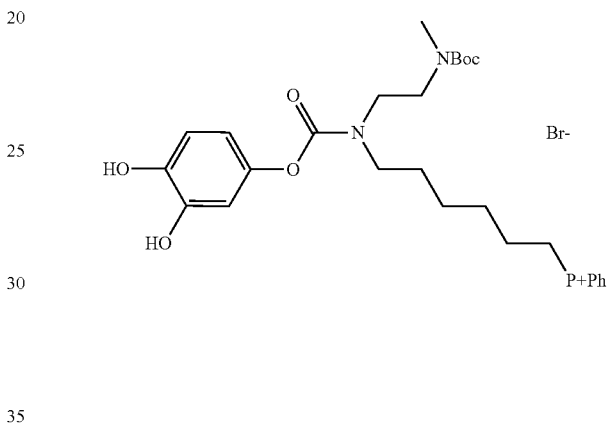

To a 100 mL RB flask, (6-(((3,4-bis(benzyloxy)-phenoxy)carbonyl)(2-((tert-butoxycarbonyl)(methyl)amino)ethyl)amino)hexyl)-triphenyl-phosphonium bromide (751 mg, 0.805 mmol), 10% Pd/C (600 mg, 0.564 mmol), EtOAc (3 mL), MeOH (3 mL), and AcOH (1 mL) was added. The mixture was stirred under an atmosphere of hydrogen. After 72 h, the mixture was filtered through Celite, and the solvents were evaporated to afford (6-(2-((tert -butoxycarbonyl)(methyl)amino)ethyl)((3,4-dihydroxyphenoxy)carbonyl)amino)hexyl)-triphenylphosphonium bromide. LCMS ($C_{39}H_{48}N_2O_6P$) (ES, m/z) 671 $[M]^+$.

Step 4: (6-((2-((tert-butoxycarbonyl)(methyl)amino)ethyl)((3,4-diacetoxyphenoxy)carbonyl)amino)hexyl)-triphenylphosphonium bromide

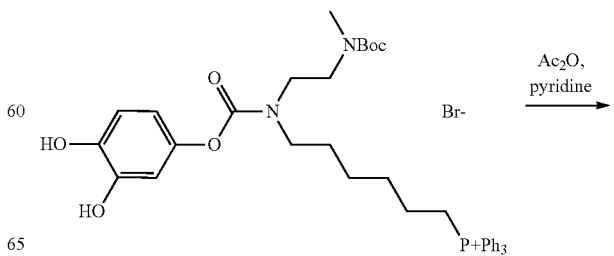

-continued

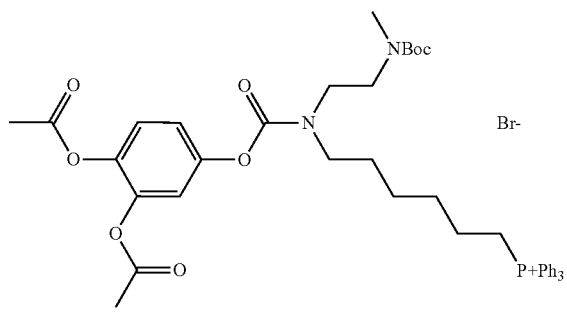

To a 20 mL vial, (6-((2-((tert-butoxycarbonyl)(methyl)amino)ethyl)((3,4-dihydroxyphenoxy)carbonyl)amino)hexyl)-triphenylphosphonium bromide (590 mg, 785 mmol), acetic anhydride (2 mL), and pyridine (2 mL) was added. The mixture was stirred at RT for 10 min. The solvents were evaporated, and the residue was co-evaporated with toluene 3 times. The residue was purified by silica gel chromatography with 0-10% MeOH in DCM as eluent to afford (6-((2-((tert-butoxycarbonyl)(methyl)amino)ethyl)((3,4-diacetoxyphenoxy)carbonyl)amino)hexyl)-triphenylphosphonium bromide. LCMS ($C_{43}H_{52}N_2O_8P$) (ES, m/z) 755 $[M]^+$.

Step 5: (6-(((3,4-diacetoxyphenoxy)carbonyl)(2-(methylamino)ethyl)amino)hexyl)triphenylphosphonium bromide 2,2,2 trifluoroacetate

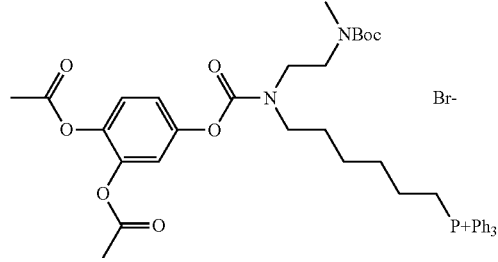

To a 20 mL vial, (6-((2-((tert-butoxycarbonyl)(methyl)amino)ethyl)((3,4-diacetoxyphenoxy)carbonyl)amino)hexyl)-triphenylphosphonium bromide (100 mg, 0.120 mmol) and TFA (2 mL) was added. The mixture was stirred for 10 min. The solvents were evaporated to afford Intermediate 11 ((6-(((3,4-diacetoxyphenoxy)carbonyl)(2-(methylamino)ethyl)amino)hexyl)-triphenylphosphonium bromide 2,2,2 trifluoroacetate). LCMS ($C_{38}H_{44}N_2O_6P$) (ES, m/z) 655 $[M]^+$.

Compound 1: 6-(4-hydroxy-3,5-dimethoxyphenoxy)benzo[d]thiazole-2-carbonitrile

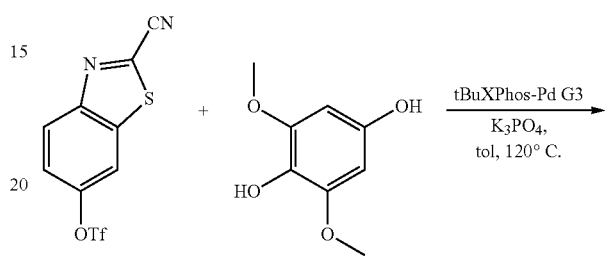

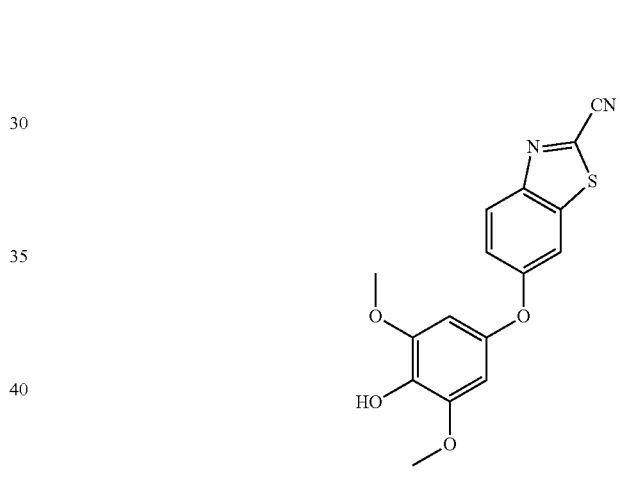

To a 20 mL vial, Intermediate 1 (100 mg, 0.324 mmol), tBuXPhos-Pd G3 (12.9 mg, 0.0162 mmol), potassium phosphate (138 mg, 0.649 mmol), 2,6-dimethoxybenzene-1,4-diol (66.2 mg, 0.389 mmol), and toluene (3 mL) was added. The mixture was sparged with nitrogen for 1 min. The mixture was stirred and heated at 120° C. for 2 h. The mixture was diluted in EtOAc (5 mL) and filtered. The solvents of the filtrate were evaporated, and the residue was purified by silica gel chromatography with 0-80% EtOAc in heptane to afford Compound 1 (6-(4-hydroxy-3,5-dimethoxyphenoxy)benzo[d]thiazole-2-carbonitrile). LCMS ($C_{16}H_{12}N_2O_4S$) (ES, m/z) 329 $[M+H]^+$. $^1$H NMR (400 MHz, DMSO-$d_6$) δ 8.37 (d, J=2.4 Hz, 1H), 8.22 (dd, J=9.1, 2.1 Hz, 1H), 7.77 (d, J=2.7 Hz, 1H), 7.41 (dd, J=9.3, 2.7 Hz, 1H), 6.51 (d, J=2.1 Hz, 2H), 3.74 (d, J=2.1 Hz, 6H).

Compounds 2-5 in the following Table 1 were prepared from Intermediate 1 or Intermediate 2 and the corresponding commercially available phenol in a manner analogous to that for the preparation of Compound 1.

TABLE 1

| Compound | Name | Structure | (ES, m/z) [M + H]+ |
|---|---|---|---|
| 2 | 6-(4-hydroxy-3-methoxyphenoxy)benzo[d]thiazole-2-carbonitrile | 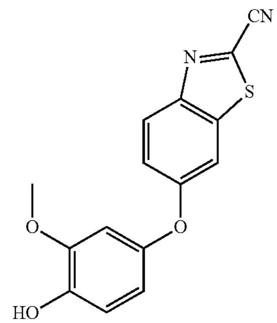 [SMILES: COc1cc(Oc2ccc3nc(C#N)sc3c2)ccc1O] | 299 |
| 3 | 6-(4-hydroxy-3,5-dimethylphenoxy)benzo[d]thiazole-2-carbonitrile | 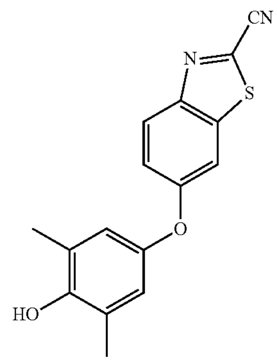 [SMILES: Cc1cc(Oc2ccc3nc(C#N)sc3c2)cc(C)c1O] | 297 |
| 4 | 5-fluoro-6-(4-hydroxy-3,5-dimethoxyphenoxy)benzo[d]thiazole-2-carbonitrile | 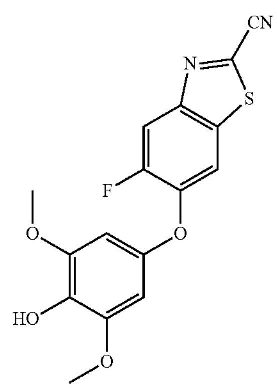 [SMILES: COc1cc(Oc2cc3sc(C#N)nc3cc2F)cc(OC)c1O] | 347 |
| 5 | 6-(2-hydroxyphenoxy)benzo[d]thiazole-2-carbonitrile | 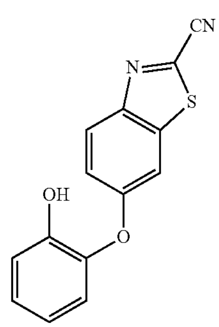 [SMILES: N#Cc1nc2ccc(Oc3ccccc3O)cc2s1] | 269 |

Compound 6: (6-(2-(5-((2-cyanobenzo[d]thiazol-6-yl)oxy)-2-hydroxy-3-methoxyphenoxy)acetamido)hexyl)triphenylphosphonium bromide Step 1: tert-butyl 2-(5-((2-cyanobenzo[d]thiazol-6-yl)oxy)-2-hydroxy-3-methoxyphenoxy)acetate

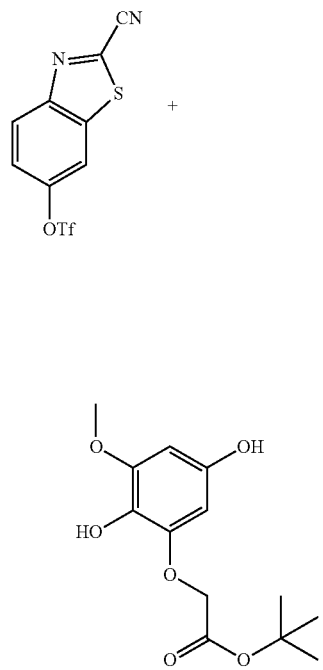

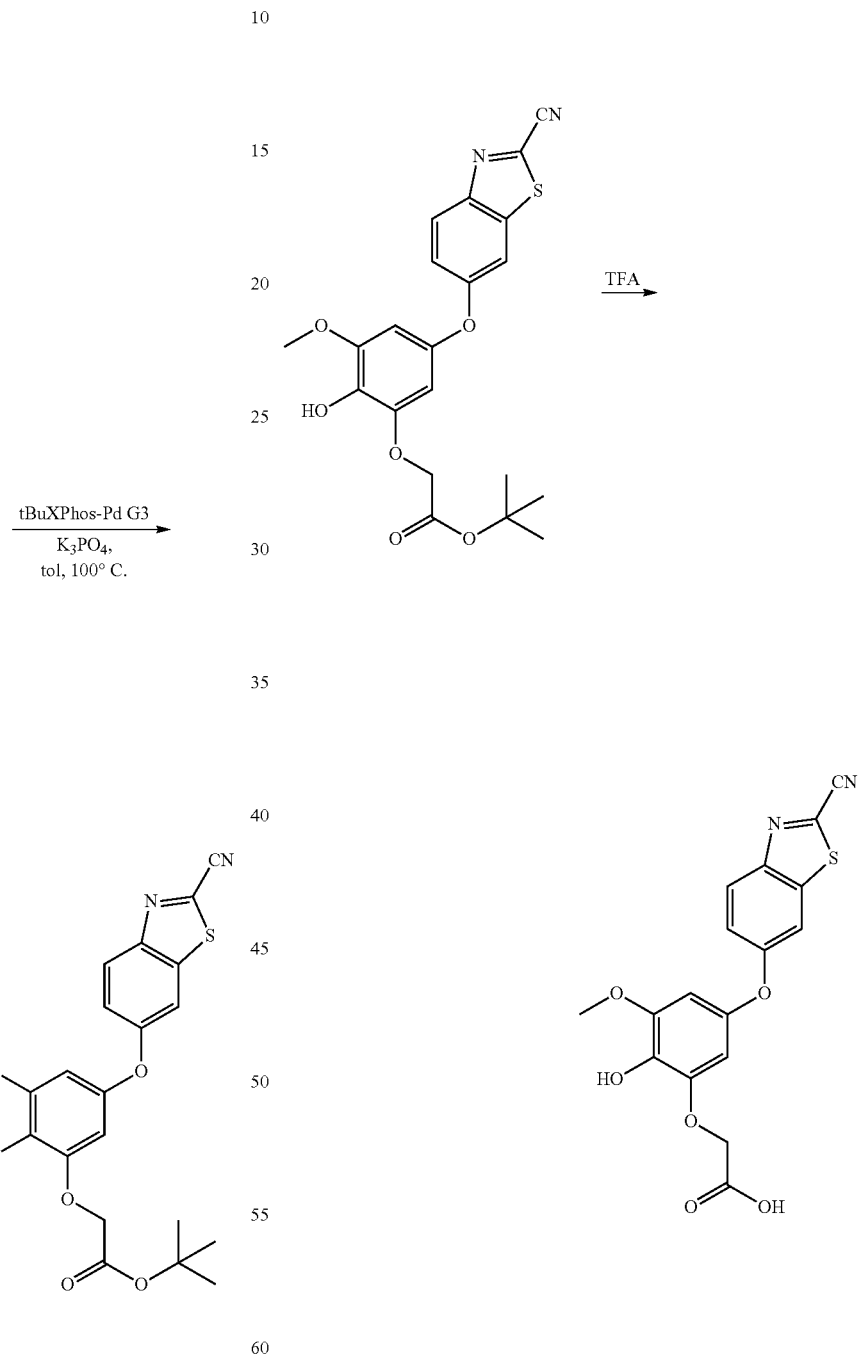

To a 20 mL vial, Intermediate 1 (49.0 mg, 0.159 mmol), Intermediate 5 (51.2 mg, 0.189 mmol), tBuXPhos-Pd G3 (6.3 mg, 0.0080 mmol), potassium phosphate (67.5 mg, 0.318 mmol), and toluene (1.5 mL) were added. The mixture was sparged with nitrogen for 1 min. The mixture was stirred and heated at 100° C. for 1 h. The mixture was adsorbed to Celite and purified by silica gel chromatography with 0-60% EtOAc in heptane to afford tert-butyl 2-(5-((2-cyanobenzo[d]thiazol-6-yl)oxy)-2-hydroxy-3-methoxyphenoxy)acetate. LCMS ($C_{21}H_{20}N_2O_6S$) (ES, m/z) 429 [M+H]$^+$.

Step 2: 2-(5-((2-cyanobenzo[d]thiazol-6-yl)oxy)-2-hydroxy-3-methoxyphenoxy)acetic acid To a 20 mL vial, tert-butyl 2-(5-((2-cyanobenzo[d]thiazol-6-yl)oxy)-2-hydroxy-3-methoxyphenoxy)acetate (42.5 mg, 0.0992 mmol) and TFA (1 mL) was added. The mixture was stirred for 30 min. The solvents were evaporated to afford 2-(5-((2-cyanobenzo[d]thiazol-6-yl)oxy)-2-hydroxy-3-methoxyphenoxy)acetic acid. LCMS ($C_{17}H_{12}N_2O_6S$) (ES, m/z) 373 [M+H]$^+$.

Step 3: (6-(2-(5-((2-cyanobenzo[d]thiazol-6-yl)oxy)-2-hydroxy-3-methoxyphenoxy)acetamido)hexyl) triphenylphosphonium bromide

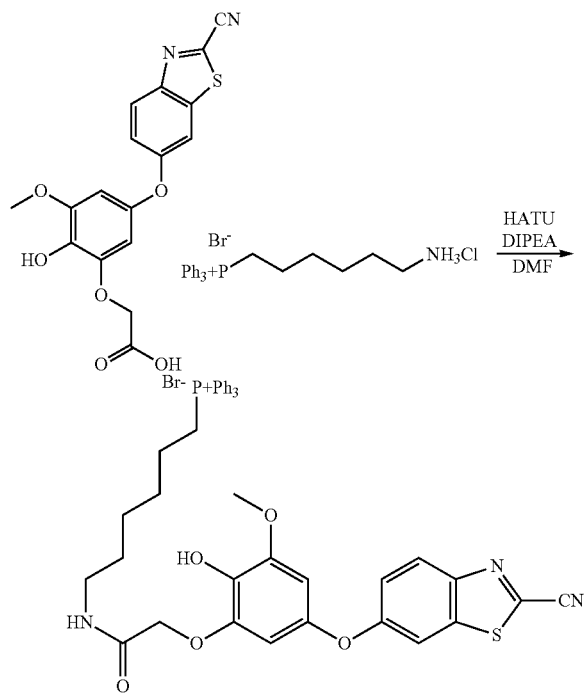

To a 20 mL vial, tert-butyl 2-(5-((2-cyanobenzo[d]thiazol-6-yl)oxy)-2-hydroxy-3-methoxyphenoxy)acetate (36.9 mg, 0.0991 mmol), (6-aminohexyl)triphenylphosphonium bromide hydrochloride (56.9 mg, 0.119 mmol), DMF (1 mL), and DIPEA (0.052 mL, 0.30 mmol) was added. The mixture was stirred. To the mixture, HATU (45.2 mg, 0.119 mmol) was added. After 1 h, the mixture was purified by reversed phase HPLC (MeCN/water w/0.1% TFA) to afford Compound 6 ((6-(2-(5-((2-cyanobenzo[d]thiazol-6-yl)oxy)-2-hydroxy-3-methoxyphenoxy)acetamido)hexyl)-triphenylphosphonium bromide). LCMS $(C_{41}H_{39}N_3O_5PS)^+$ (ES, m/z) 716 $[M]^+$. $^1$H NMR (400 MHz, DMSO-$d_6$) δ 8.66 (s, 1H), 8.26 (s, 1H), 8.21 (dd, J=9.2, 2.7 Hz, 1H), 7.90 (q, J=4.6, 2.9 Hz, 3H), 7.78 (td, J=7.9, 6.4, 3.6 Hz, 13H), 7.38 (dt, J=8.6, 3.0 Hz, 1H), 6.54 (dt, J=12.7, 3.1 Hz, 2H), 4.42 (d, J=2.7 Hz, 2H), 3.74 (d, J=2.7 Hz, 3H), 3.63-3.47 (m, 2H), 3.12 (d, J=6.8 Hz, 2H), 1.61-1.19 (m, 8H).

Compounds 7-9 in the following Table 2 were prepared from Intermediate 1 and the corresponding phenol Intermediates 3-5 in a manner analogous to that for the preparation of Compound 6.

TABLE 2

| Compound | Name | Structure | (ES, m/z) $[M]^+$ |
|---|---|---|---|
| 7 | (6-(2-(4-((2-cyanobenzo[d]thiazol-6-yl)oxy)-3-hydroxyphenoxy)acetamido)hexyl) triphenylphosphonium bromide | 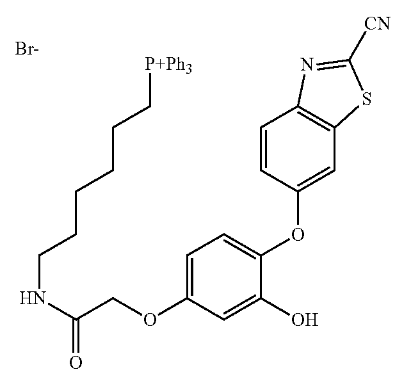 | 686 |

TABLE 2-continued

| Compound | Name | Structure | (ES, m/z) [M]+ |
|---|---|---|---|
| 8 | (6-(2-(3-((2-cyanobenzo[d]thiazol-6-yl)oxy)-4-hydroxyphenoxy)acetamido)hexyl)triphenylphosphonium bromide | Br– | 686 |
| 9 | (6-(2-(5-((2-cyanobenzo[d]thiazol-6-yl)oxy)-2-hydroxyphenoxy)acetamido)hexyl)triphenylphosphonium bromide | Br– | 686 |

Compound 10: (S)-2-(6-(4-hydroxy-3,5-dimethoxyphenoxy)benzo[d]thiazol-2-yl)-4,5-dihydrothiazole-4-carboxylic acid

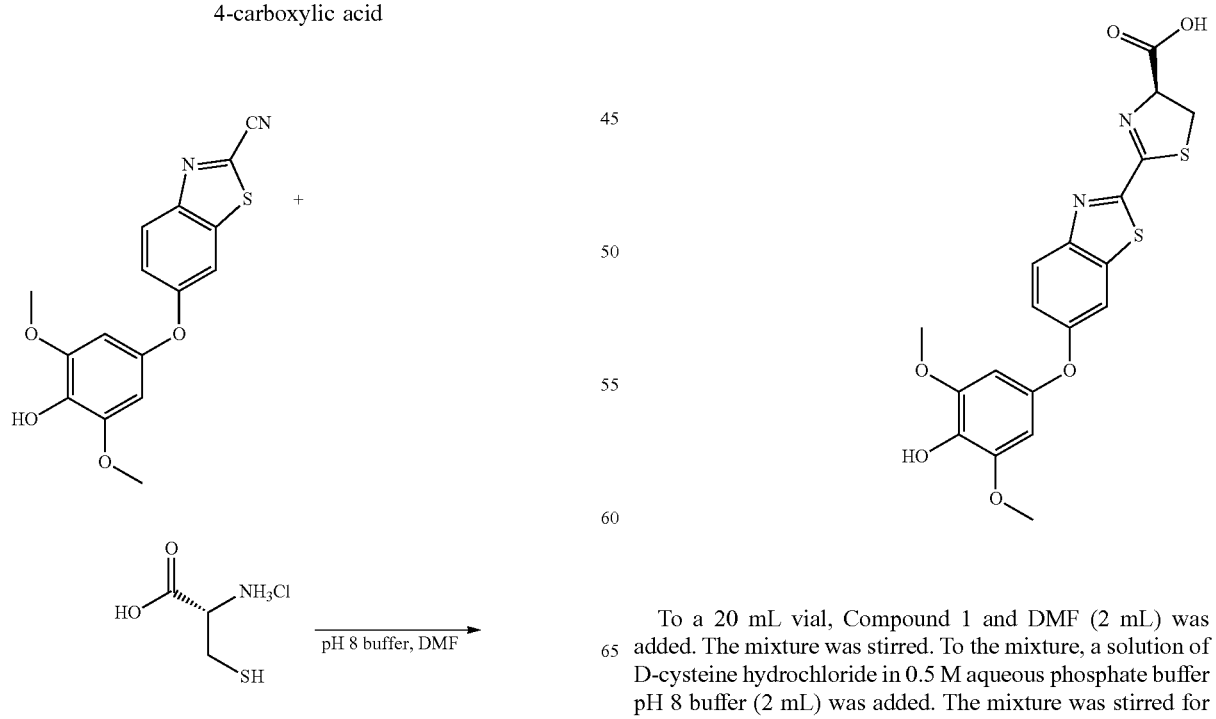

To a 20 mL vial, Compound 1 and DMF (2 mL) was added. The mixture was stirred. To the mixture, a solution of D-cysteine hydrochloride in 0.5 M aqueous phosphate buffer pH 8 buffer (2 mL) was added. The mixture was stirred for 30 min. The mixture was purified by reversed phase HPLC (MeCN/water w/0.1% TFA) to afford Compound 10 ((S)-2-(6-(4-hydroxy-3,5-dimethoxyphenoxy)benzo[d]thiazol-2-yl)-4,5-dihydrothiazole-4-carboxylic acid). LCMS ($C_{19}H_{16}N_2O_6S_2$) (ES, m/z) 433 [M+H]$^+$. $^1$H NMR (400 MHz, DMSO-d$_6$) δ 13.21 (s, 1H), 8.33 (s, 1H), 8.12 (dd, J=9.0, 3.1 Hz, 1H), 7.65 (s,1H), 7.27 (dd, J=9.3, 3.8 Hz, 1H), 6.50 (s, 2H), 5.43 (t, J=9.1 Hz, 1H), 3.77 (d, J=10.7 Hz, 1H), 3.73 (d, J=2.9 Hz, 6H), 3.68 (d, J=10.1 Hz, 1H).

Compounds 11-15 in the following Table 3 were prepared from the corresponding cyanobenzothiazole Compounds 2-6 and D-cysteine in a manner analogous to that for the preparation of Compound 10.

TABLE 3

| Compound | Name | Structure | (ES, m/z) [M + H]$^+$ |
|---|---|---|---|
| 11 | (S)-2-(6-(4-hydroxy-3-methoxyphenoxy)benzo[d]thiazol-2-yl)-4,5-dihydrothiazole-4-carboxylic acid | 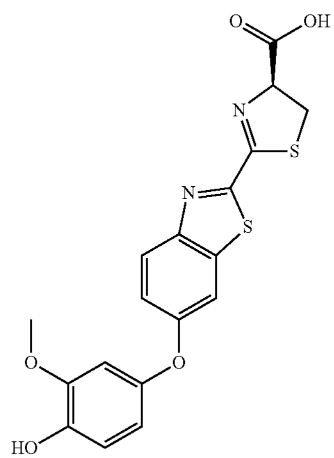 [SMILES: COc1cc(Oc2ccc3nc(C4=N[C@@H](C(=O)O)CS4)sc3c2)ccc1O] | 403 |
| 12 | (S)-2-(6-(4-hydroxy-3,5-dimethylphenoxy)benzo[d]thiazol-2-yl)-4,5-dihydrothiazole-4-carboxylic acid | 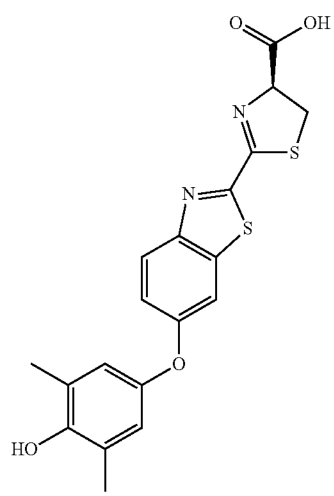 [SMILES: Cc1cc(Oc2ccc3nc(C4=N[C@@H](C(=O)O)CS4)sc3c2)cc(C)c1O] | 401 |
| 13 | (S)-2-(5-fluoro-6-(4-hydroxy-3,5-dimethoxyphenoxy)benzo[d]thiazol-2-yl)-4,5-dihydrothiazole-4-carboxylic acid | 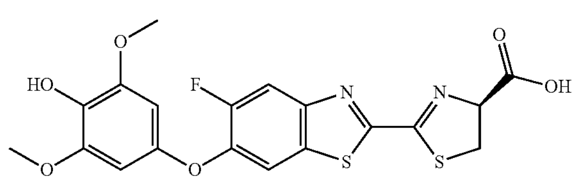 [SMILES: COc1cc(Oc2cc3sc(C4=N[C@@H](C(=O)O)CS4)nc3cc2F)cc(OC)c1O] | 451 |
| 14 | (S)-2-(6-(2-hydroxyphenoxy)benzo[d]thiazol-2-yl)-4,5-dihydrothiazole-4-carboxylic acid | 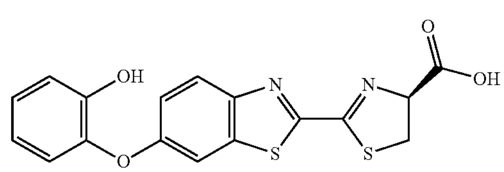 [SMILES: O=C(O)[C@H]1CSC(c2nc3ccc(Oc4ccccc4O)cc3s2)=N1] | 373 |

| Compound | Name | Structure | (ES, m/z) [M + H]+ |
|---|---|---|---|
| 15 | (S)-(6-(2-(5-((2-(4-carboxy-4,5-dihydrothiazol-2-yl)benzo[d]thiazol-6-yl)oxy)-2-hydroxy-3-methoxyphenoxy)acetamido)hexyl)triphenylphosphonium bromide | 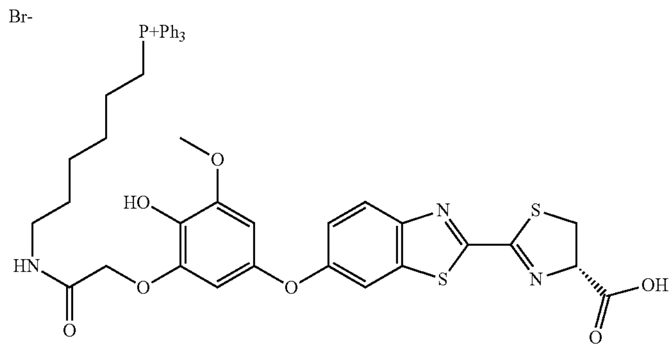 | 820 [M]+ |

Compound 16: (S)-(6-(2-(2-hydroxy-3-methoxy-5-((2-(4-(methoxycarbonyl)-4,5-dihydrothiazol-2-yl)benzo[d]thiazol-6-yl)oxy)phenoxy)acetamido)hexyl)triphenylphosphonium bromide To a 4 mL vial containing Compound 6 ((6-(2-(5-((2-cyanobenzo[d]thiazol-6-yl)oxy)-2-hydroxy-3-methoxyphenoxy)acetamido)hexyl)triphenylphosphonium bromide) (15.8 mg, 0.0198 mmol), DMF (1 mL) was added. The mixture was stirred. To the mixture, a solution of methyl D-cysteinate (3.2 mg, 0.024 mmol) in pH 8 0.5 M phosphate buffer (0.5 mL) was added. After 30 min, the mixture was purified by reversed phase HPLC (MeCN/water w/0.1% TFA) to afford Compound 16 ((S)-(6-(2-(2-hydroxy-3-methoxy-5-((2-(4-(methoxycarbonyl)-4,5-dihydrothiazol-2-yl)benzo[d]thiazol-6-yl)oxy)phenoxy)acetamido)hexyl)triphenylphosphonium bromide). LCMS $(C_{45}H_{45}N_3O_7PS_2)^+$ (ES, m/z) 834 [M]+. $^1$H NMR (400 MHz, DMSO-$d_6$) δ 8.63 (s, 1H), 8.26 (d, J=6.2 Hz, 1H), 8.16-8.09 (m, 1H), 7.89 (d, J=7.0 Hz, 3H), 7.78 (q, J=6.1, 5.0 Hz, 13H), 7.62 (d, J=3.2 Hz, 1H), 7.32-7.22 (m, 1H), 6.53 (d, J=11.3 Hz, 2H), 5.53 (t, J=9.2 Hz, 1H), 4.42 (s, 2H), 3.82 (t, J=10.6 Hz, 1H), 3.77-3.72 (m, 6H), 3.69 (d, J=10.4 Hz, 1H), 3.12 (q, J=6.9 Hz, 2H), 1.51-1.25 (m, 8H).

Compound 17: (S)-2-(6-(4-hydroxyphenoxy)benzo[d]thiazol-2-yl)-4,5-dihydrothiazole-4-carboxylic acid Step 1: (Z)-N-(2-bromo-4-fluorophenyl)-4-chloro-5H-1,2,3-dithiazol-5-imine 2-bromo-4-fluoroaniline (2.00 g, 10.5 mmol) was dissolved in dichloromethane (50 mL). 5-dichloro-1,2,3-dithiazolium chloride (Appel's salt, 2.63 g, 12.6 mmol) was added, and the reaction mixture was stirred overnight. The reaction mixture was then extracted with dichloromethane/water. The organic layer was collected and concentrated to an orange oil, which was used directly in the next step.

Step 2: 6-fluorobenzo[d]thiazole-2-carbonitrile

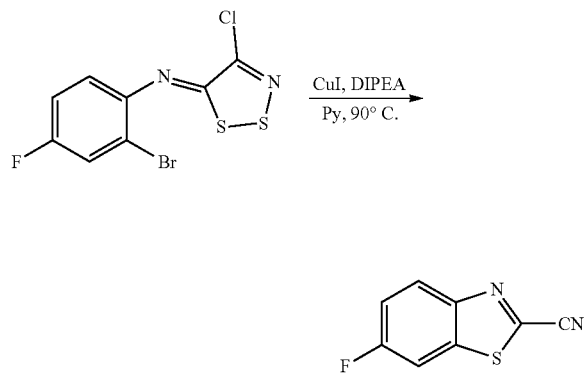

(Z)-N-(2-bromo-4-fluorophenyl)-4-chloro-5H-1,2,3-dithiazol-5-imine (0.26 g, 0.80 mmol) was dissolved in anhydrous pyridine (10 mL). Copper iodide (0.18 g, 0.90 mmol) and DIPEA (0.28 mL, 1.6 mmol) were added, and the reaction was heated at 90° C. for one hour. The mixture was concentrated, and the residue was extracted with ethyl acetate/water. The organic layer was collected and concentrated. The resulting residue was purified by flash chromatography on silica gel. $^1$H NMR (300 MHz, CD2Cl$_2$) δ 8.22 (m, 1H), 7.71 (m, 1H), 7.44 (m, 1H); FNMR (300 MHz, CD$_2$Cl$_2$) δ 110.91.

Step 3: 6-(4-methoxyphenoxy)benzo[d]thiazole-2-carbonitrile

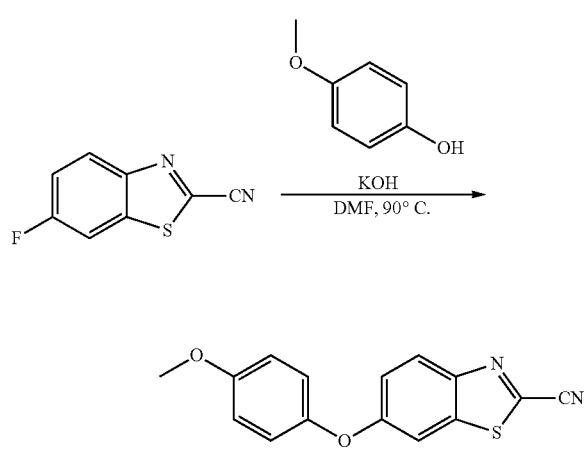

4-methoxyphenol (60 mg, 0.48 mmol) was dissolved in equal molar of potassium hydroxide aqueous solution. The water was removed by lyophilization. The resulting solid was resuspended in DMF (10 mL). 6-fluorobenzo[d]thiazole-2-carbonitrile (10 mg, 0.056 mmol) was added, and the resulting solution was transferred to a microwave tube and reacted at 90° C., 90 W for 10 min. (CEM Discovery Synthesizer). The reaction mixture was then purified by reversed phase HPLC to afford 6-(4-methoxyphenoxy)benzo[d]thiazole-2-carbonitrile.

Step 4: (S)-2-(6-(4-hydroxyphenoxy)benzo[d]thiazol-2-yl)-4,5-dihydrothiazole -4-carboxylic acid

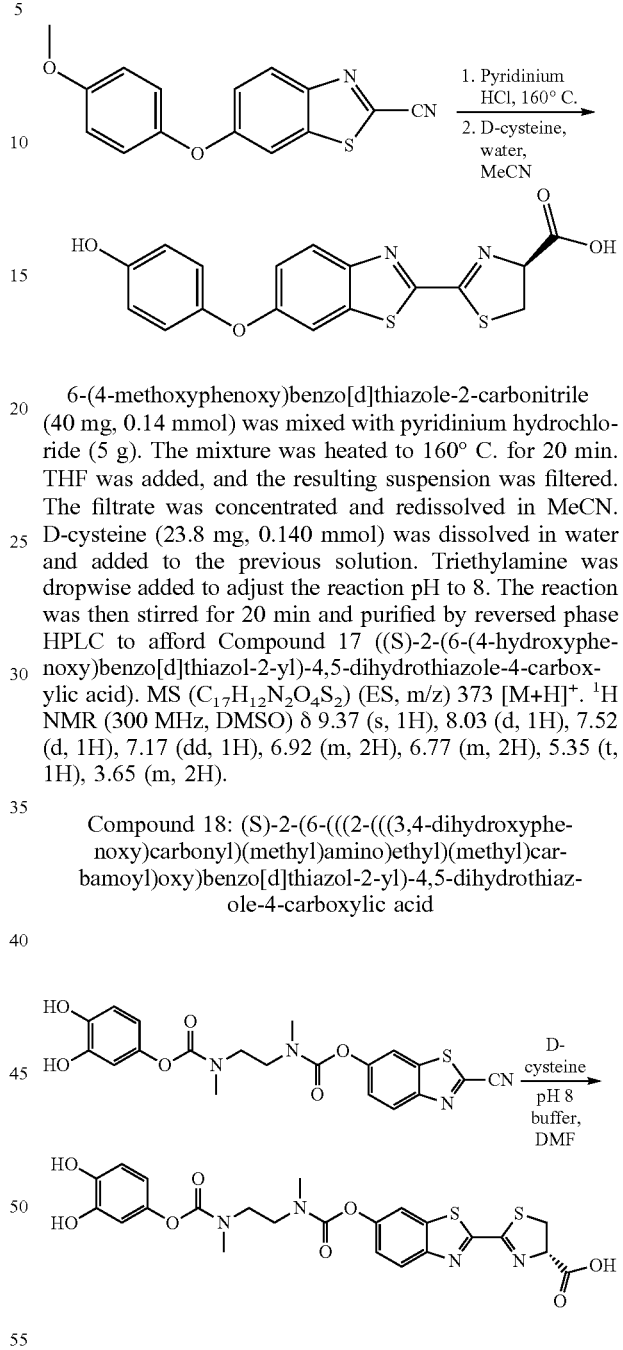

6-(4-methoxyphenoxy)benzo[d]thiazole-2-carbonitrile (40 mg, 0.14 mmol) was mixed with pyridinium hydrochloride (5 g). The mixture was heated to 160° C. for 20 min. THF was added, and the resulting suspension was filtered. The filtrate was concentrated and redissolved in MeCN. D-cysteine (23.8 mg, 0.140 mmol) was dissolved in water and added to the previous solution. Triethylamine was dropwise added to adjust the reaction pH to 8. The reaction was then stirred for 20 min and purified by reversed phase HPLC to afford Compound 17 ((S)-2-(6-(4-hydroxyphenoxy)benzo[d]thiazol-2-yl)-4,5-dihydrothiazole-4-carboxylic acid). MS (C$_{17}$H$_{12}$N$_2$O$_4$S$_2$) (ES, m/z) 373 [M+H]$^+$. $^1$H NMR (300 MHz, DMSO) δ 9.37 (s, 1H), 8.03 (d, 1H), 7.52 (d, 1H), 7.17 (dd, 1H), 6.92 (m, 2H), 6.77 (m, 2H), 5.35 (t, 1H), 3.65 (m, 2H).

Compound 18: (S)-2-(6-(((2-(((3,4-dihydroxyphenoxy)carbonyl)(methyl)amino)ethyl)(methyl)carbamoyl)oxy)benzo[d]thiazol-2-yl)-4,5-dihydrothiazole-4-carboxylic acid To a 20 mL vial, Intermediate 10 (21.0 mg, 0.0475 mmol) and DMF (2 mL) was added. The mixture was stirred. To this mixture, D-cysteine (6.9 mg, 0.057 mmol) in pH 8 buffer (2 mL) was added. The mixture was stirred for 2 hours. The mixture was purified by reversed phase HPLC (MeCN/water w/0.1% TFA) to afford to afford Compound 18 ((S)-2-(6-(((2-(((3,4-dihydroxyphenoxy)carbonyl)(methyl)amino)ethyl)(methyl)carbamoyl)oxy)benzo[d]thiazol-2-yl)-4,5-dihydrothiazole-4-carboxylic acid). LCMS (C$_{23}$H$_{22}$N$_4$O$_8$S$_2$) (ES, m/z) 547 [M+H]$^+$. $^1$H NMR (400 MHz, DMF-d$_7$) δ 13.91 (s, 1H), 9.51 (d, J=3.8 Hz, 1H), 9.26 (d, J=19.5 Hz, 1H), 8.36 (dd, J=15.4, 8.8 Hz, 1H), 7.73-7.53

(m, 1H), 7.02-6.78 (m, 3H), 6.63 (dddd, J=17.9, 14.8, 8.5, 2.6 Hz, 1H), 5.75 (t, J=9.4 Hz, 1H), 4.14-3.92 (m, 6H), 3.39-3.17 (m, 6H).

Compound 19: methyl (S)-2-(6-(((2-(((3,4-dihydroxyphenoxy)carbonyl)(methyl)amino)ethyl)(methyl)carbamoyl)oxy)benzo[d]thiazol-2-yl)-4,5-dihydrothiazole-4-carboxylate

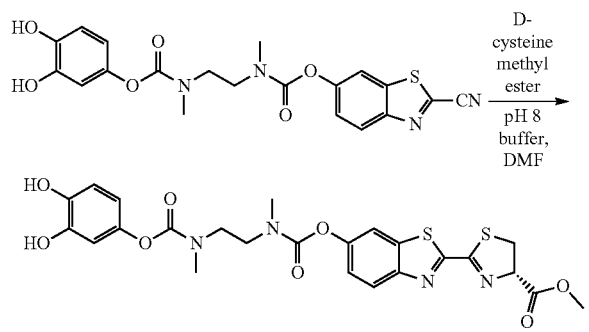

To a 20 mL vial, Intermediate 10 (27.6 mg, 0.0475 mmol) and DMF (2 mL) was added. The mixture was stirred. To the mixture, D-cysteine methyl ester (10.1 mg, 0.749 mmol) in pH 8 buffer (2 mL) was added. The mixture was stirred for 2 hours. The mixture was purified by reversed phase HPLC (MeCN/water w/0.1% TFA) to afford to afford Compound 19 (methyl (S)-2-(6-(((2-(((3,4-dihydroxyphenoxy)carbonyl)(methyl)amino)ethyl)(methyl)carbamoyl)oxy)benzo[d]thiazol-2-yl)-4,5-dihydrothiazole-4-carboxylate). LCMS ($C_{24}H_{24}N_4O_8S_2$) (ES, m/z) 561 [M+H]$^+$. $^1$H NMR (400 MHz, DMSO-d$_6$) δ 9.07 (d, J=16.4 Hz, 1H), 8.84 (d, J=9.7 Hz, 1H), 8.16 (dt, J=10.2, 5.8 Hz, 1H), 8.04-7.81 (m, 1H), 7.35 (dd, J=25.8, 8.6 Hz, 1H), 6.66 (dd, J=18.3, 8.4 Hz, 1H), 6.49 (dd, J=20.3, 9.8 Hz, 1H), 6.32 (td, J=21.6, 18.0, 8.4 Hz, 1H), 5.57 (t, J=9.6 Hz, 1H), 3.85 (t, J=10.6 Hz, 1H), 3.77 (d, J=2.5 Hz, 3H), 3.74-3.51 (m, 5H), 3.20-2.88 (m, 6H).

Compound 20: (S)-4-(((2-((((2-(4-(methoxycarbonyl)-4,5-dihydrothiazol-2-yl)benzo[d]thiazol-6-yl)oxy)carbonyl)(methyl)amino)ethyl)(methyl)carbamoyl)oxy)-1,2-phenylene diacetate Step 1: 4-(((2-((((2-cyanobenzo[d]thiazol-6-yl)oxy)carbonyl)(methyl)amino)ethyl)(methyl)carbamoyl)oxy)-1,2-phenylene diacetate

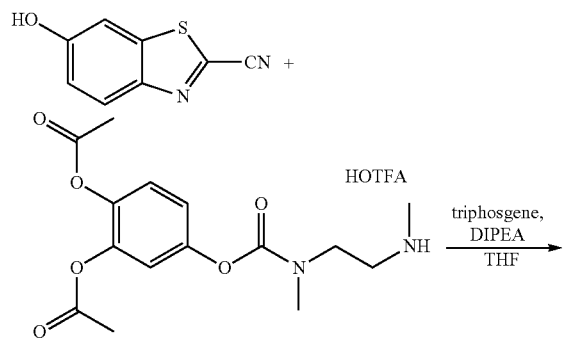

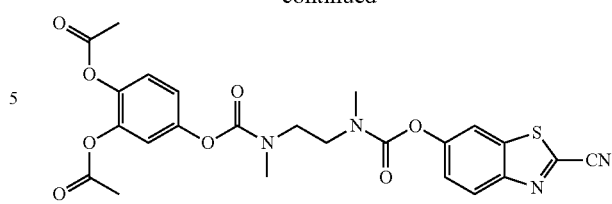

To a 20 mL vial, 6-hydroxybenzo[d]thiazole-2-carbonitrile (18.0 mg, 0.102 mmol), THF (1.5 mL), and DIPEA (0.073 mL, 0.41 mmol) was added. The mixture was added dropwise to a stirring solution of triphosgene (12.8 mg, 0.0431 mmol) in THF (1 mL) over 1 min. After 5 min, to the mixture was added the Intermediate 9 (43.1 mg, 0.132 mmol) in THF (1 mL). After 20 min, the mixture was adsorbed to Celite and purified by silica gel chromatography with 0-100% EtOAc in heptane as eluent to afford 4-(((2-((((2-cyanobenzo[d]thiazol-6-yl)oxy)carbonyl)-(methyl)amino)ethyl)(methyl)carbamoyl)oxy)-1,2-phenylene diacetate. LCMS ($C_{24}H_{22}N_4O_8S$) (ES, m/z) 527 [M+H]$^+$.

Step 2: (S)-4-(((2-((((2-(4-(methoxycarbonyl)-4,5-dihydrothiazol-2-yl)benzo[d]thiazol-6-yl)oxy)carbonyl)(methyl)amino)ethyl)(methyl)carbamoyl)oxy)-1,2-phenylene diacetate

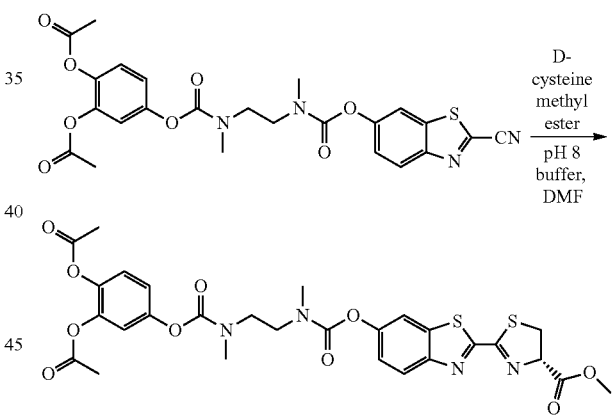

To a 20 mL vial, -(((2-((((2-cyanobenzo[d]thiazol-6-yl)oxy)carbonyl) -(methyl)amino)ethyl)(methyl)carbamoyl)oxy)-1,2-phenylene diacetate (38.4 mg, 0.0729 mmol) and DMF (2 mL) was added. The mixture was stirred. To this mixture, D-cysteine methyl ester (11.8 mg, 0.875 mmol) in pH 8 buffer (2 mL) was added. The mixture was stirred for 2 hours. The mixture was purified by reversed phase HPLC (MeCN/water w/0.1% TFA) to afford Compound 20 ((S)-4-(((2-((((2-(4-(methoxycarbonyl)-4,5-dihydrothiazol-2-yl)benzo[d]thiazol-6-yl)oxy)carbonyl)(methyl)amino)ethyl)(methyl)carbamoyl)oxy)-1,2-phenylene diacetate). LCMS ($C_{28}H_{28}N_4O_{10}S_2$) (ES, m/z) 645 [M+H]$^+$. $^1$H NMR (400 MHz, DMSO-d$_6$) δ 8.16 (td, J=11.2, 10.5, 4.7 Hz, 1H), 7.97 (dd, J=28.4, 15.3 Hz, 1H), 7.52-7.21 (m, 2H), 7.19-6.86 (m, 2H), 5.58 (t, J=8.8 Hz, 1H), 3.85 (t, J=10.7 Hz, 1H), 3.77 (d, J=2.9 Hz, 3H), 3.74-3.62 (m, 5H), 3.19-2.96 (m, 6H), 2.31-2.20 (m, 6H).

Compound 21: (6-((2-((((2-cyanobenzo[d]thiazol-6-yl)oxy)carbonyl)(methyl)amino)ethyl) -((3,4-diacetoxyphenoxy)carbonyl)amino)hexyl)triphenylphosphonium bromide

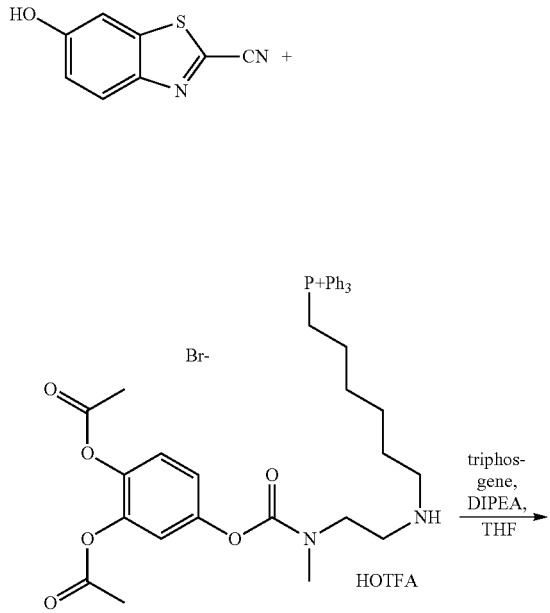

To a 20 mL vial, 6-hydroxybenzo[d]thiazole-2-carbonitrile (20.0 mg, 0.114 mmol), THF (1.5 mL), and DIPEA (0.100 mL, 0.568 mmol) was added. The mixture was added dropwise to a stirring solution of triphosgene (16.8 mg, 0.0568 mmol) in THF (1 mL) over 1 min. After 5 min, to the mixture was added Intermediate 11 (87.7 mg, 0.119 mmol) in THF (1 mL). After 20 min, the mixture was concentrated and purified by reversed phase HPLC (MeCN/water w/0.1% TFA) to afford Compound 21 ((6-((2-((((2-cyanobenzo[d]thiazol-6-yl)oxy)carbonyl)(methyl)amino)ethyl)-((3,4-diacetoxyphenoxy)carbonyl)amino)hexyl)triphenylphosphonium bromide). LCMS ($C_{47}H_{46}N_4O_8PS$) (ES, m/z) 857 $[M]^+$. $^1H$ NMR (400 MHz, Acetonitrile-$d_3$) δ 8.18 (td, J=9.4, 9.0, 6.0 Hz, 1H), 7.95-7.78 (m, 4H), 7.74-7.65 (m, 12H), 7.50-7.31 (m, 1H), 7.24-6.82 (m, 3H), 3.77-3.29 (m, 6H), 3.15 (p, J=7.4 Hz, 3H), 3.03 (d, J=6.5 Hz, 2H), 2.29-2.20 (m, 6H), 1.69-1.28 (m, 10H).

Compound 22: (S)-(6-((((2-(4-carboxy-4,5-dihydrothiazol-2-yl)benzo[d]thiazol-6-yl)oxy)carbonyl)(2-(((3,4-diacetoxyphenoxy)carbonyl)(methyl)amino)ethyl)amino)hexyl)triphenylphosphonium bromide

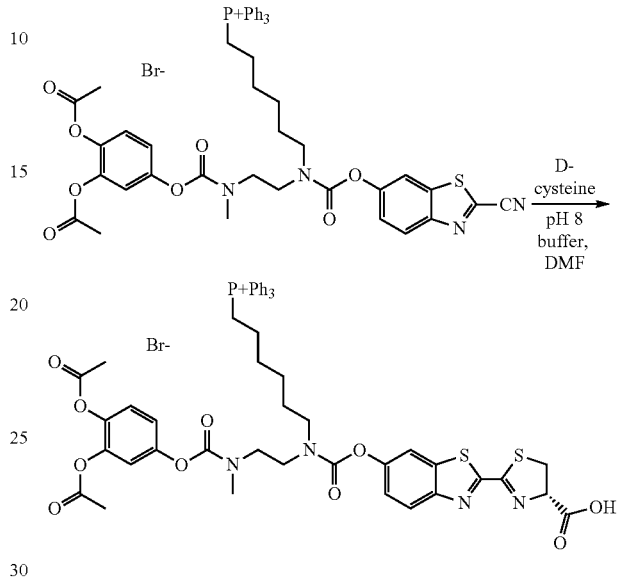

To a 8 mL vial containing Compound 21 (10.0 mg, 0.0107 mmol), DMF (1.5 mL) was added. The mixture was stirred. To this mixture, a solution of D-cysteine (1.7 mg, 0.014 mmol) in pH 8 buffer (0.5 mL) was added. The mixture was purified by reversed phase HPLC (MeCN/water w/0.5% TFA) to afford Compound 22 ((S)-(6-((((2-(4-carboxy-4,5-dihydrothiazol-2-yl)benzo[d]thiazol-6-yl)oxy)carbonyl)(2-(((3,4-diacetoxyphenoxy)carbonyl)(methyl)amino)ethyl)-amino)hexyl)triphenylphosphonium bromide). LCMS ($C_{50}H_{50}N_4O_{10}PS_2$) (ES, m/z) 961 $[M]^+$. $^1H$ NMR (400 MHz, DMF-$d_7$) δ 14.0 (br s, 1H), 8.39-8.26 (m, 1H), 8.17-8.08 (m, 9H), 8.04-7.96 (m, 6H), 7.69-7.30 (m, 3H), 5.75 (t, J=9.1 Hz, 1H), 4.16-4.00 (m, 2H), 3.51-3.22 (m, 6H), 2.54-2.44 (m, 6H), 2.01-1.69 (m, 8H), 1.68-1.53 (m, 2H).

Compound 23: (S)-(6-((2-(((3,4-diacetoxyphenoxy)carbonyl)(methyl)amino)ethyl)(((2-(4-(methoxycarbonyl)-4,5-dihydrothiazol-2-yl)benzo[d]thiazol-6-yl)oxy)carbonyl)amino)hexyl)triphenylphosphonium bromide

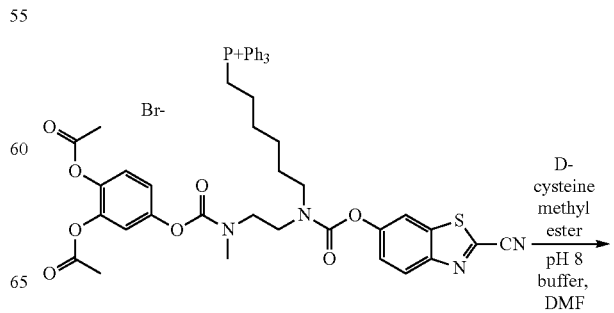

-continued

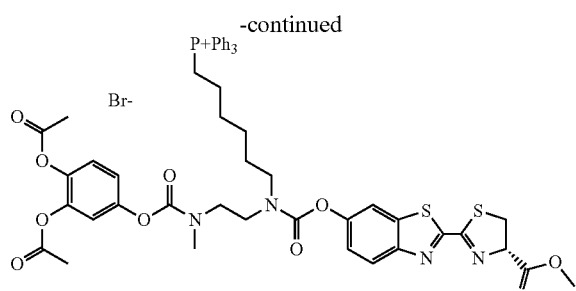

To a 8 mL vial containing Compound 21 (19.8 mg, 0.0211 mmol), DMF (1.5 mL) was added. The mixture was stirred. To this mixture, a solution of D-cysteine methyl ester (1.7 mg, 0.014 mmol) in pH 8 buffer (0.5 mL) was added. The mixture was purified by reversed phase HPLC (MeCN/water w/0.5% TFA) to afford Compound 23 (((S)-(6-((2-(((3,4-diacetoxyphenoxy)carbonyl)(methyl)amino)ethyl)(((2-(4-(methoxycarbonyl)-4,5-dihydrothiazol-2-yl)benzo[d]thiazol-6-yl)oxy)carbonyl)amino)hexyl) triphenylphosphonium bromide). LCMS ($C_{51}H_{52}N_4O_{10}PS_2$) (ES, m/z) 975 [M]$^+$. $^1$H NMR (400 MHz, DMSO-$d_6$) δ 8.15 (td, J=9.4, 4.4 Hz, 1H), 8.01-7.85 (m, 4H), 7.75 (td, J=9.7, 8.2, 5.4 Hz, 12H), 7.39-7.18 (m, 2H), 7.14 -6.81 (m, 2H), 5.57 (t, J=9.2 Hz, 1H), 3.85 (t, J=10.6 Hz, 1H), 3.77 (s, 3H), 3.41-3.23 (m, 4H), 3.05 (dd, J=55.3, 8.7 Hz, 3H), 2.31-2.10 (m, 6H), 1.65-1.26 (m, 10H).

Example 2: Cell-Free Detection of and Specificity for Superoxide

Figure 3:
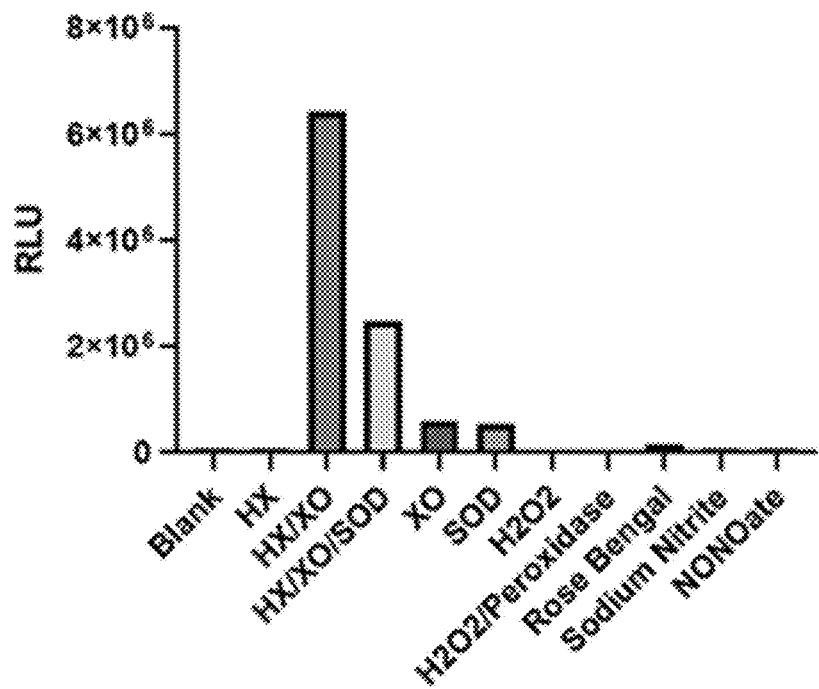
FIG. 3 shows data from assays to detect superoxide in cell-free samples, as described in Example 2.

The superoxide probe, Compound 1 (6-(4-hydroxy-3,5-dimethoxyphenoxy)benzo[d]thiazole-2-carbonitrile), was diluted into PBS to 25 µM into wells of a 96-well white-walled assay plate. Subsequently, generators of reactive oxygen and nitrogen species were diluted in PBS and added to the assay plate. The plate mixed using an orbital plate shaker for 5 minutes followed by a 30-minute incubation at room temperature protected from light. For luciferin detection, the luciferin-utilizing luciferase enzyme, UltraGlo (Promega Corporation), was prepared by mixing Luciferin Detection Reagent (Promega), Reconstitution Buffer (Promega), and d-Cysteine (Promega), and one volume was added to the reaction. The plate was mixed using an orbital plate shaker, and luminescence was measured using a GloMax® luminometer. Data are shown in FIG. 3; the blank includes PBS only; HX=hypoxanthine; XO=xanthine oxidase; and SOD=superoxide dismutase. The data demonstrate the presence of a strong signal in the presence of HX and XO, which are known to react to generate superoxide. This signal decreased in the presence of superoxide dismutase, confirming that superoxide is the source of the signal. Little to no signal was detected in the presence of hydrogen peroxide, Rose Bengal (which generates singlet oxygen), sodium nitrite, or NONOate.

Example 3: Detection of Superoxide in Cells

Figure 4:
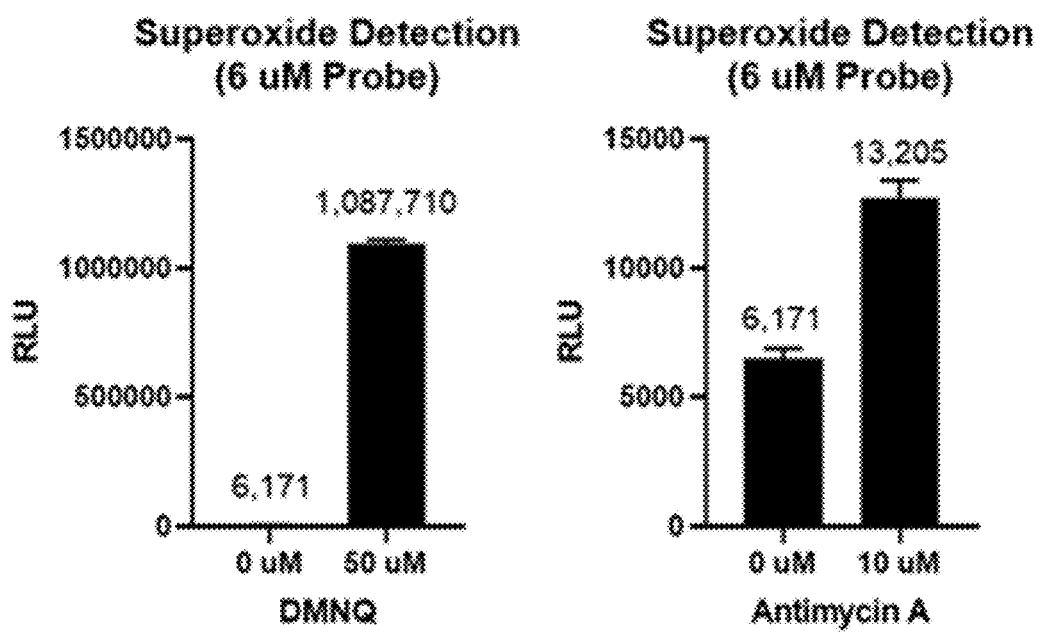
FIG. 4 shows data from assays to detect superoxide in cells upon treatment with superoxide-generating drug compounds dimethoxynaphthoquinone (DMNQ) and antimycin A, as described in Example 3.

Human hepatocarcinoma cells (Hep G2) were plated into wells of 96-well white-walled assay tissue culture plates. Plated cells were incubated overnight in a humidified tissue culture incubator at 37° C. with 5% $CO_2$. The following day the superoxide probe, Compound 1 (6-(4-hydroxy-3,5-dimethoxyphenoxy)benzo[d]thiazole-2-carbonitrile), was added to the cells in culture medium at a final concentration of 12.5 uM. Subsequently, dimethoxynaphthoquinone (DMNQ; 50 µM) or antimycin A (10 µM) diluted in culture medium was added to the reaction wells and the assay plate(s) were incubated for 1 hour in a humidified tissue culture incubator at 37° C. with 5% C02. For luciferin detection, the luciferin-utilizing luciferase enzyme, UltraGlo (Promega Corporation), was prepared by mixing Luciferin Detection Reagent (Promega), Reconstitution Buffer (Promega), and d-Cysteine (Promega), and one volume was added to the reaction. The plate was mixed using an orbital plate shaker, and luminescence was measured using a GloMax® luminometer. Data are shown in FIG. 4. An increase in signal was detected when cells were treated with either dimethoxynaphthoquinone (DMNQ) or antimycin A, both of which are known to induce formation of superoxide.

Example 4: Detection of Xanthine Oxidase In Vitro

Xanthine oxidase (XO) is an enzyme that catalyzes the oxidation of hypoxanthine or xanthine to uric acid and superoxide. XO is normally found in liver and jejunum and plays an important role in the catabolism of purines. During severe liver damage, xanthine oxidase is released into blood and can be used as a marker for liver damage. Here is shown an example of measuring xanthine oxidase activity using pro-luciferin compounds described herein. Purified xanthine oxidase was 3× fold serially diluted in 0.1M Tris (pH7.5). 25 µl of diluted enzyme was transferred into wells of a 96-well assay plate, and the reaction was started by adding 25 µl of 300 µM xanthine and 25 µl of 75 µM Compound 20. After 10, 20, 30, and 60 minutes incubations at 37° C., 75 µl of Luciferin Detection Reagent containing esterases was added to the samples, and luminescence was read after additional 20 minutes incubation at room temperature.

Figure 5:
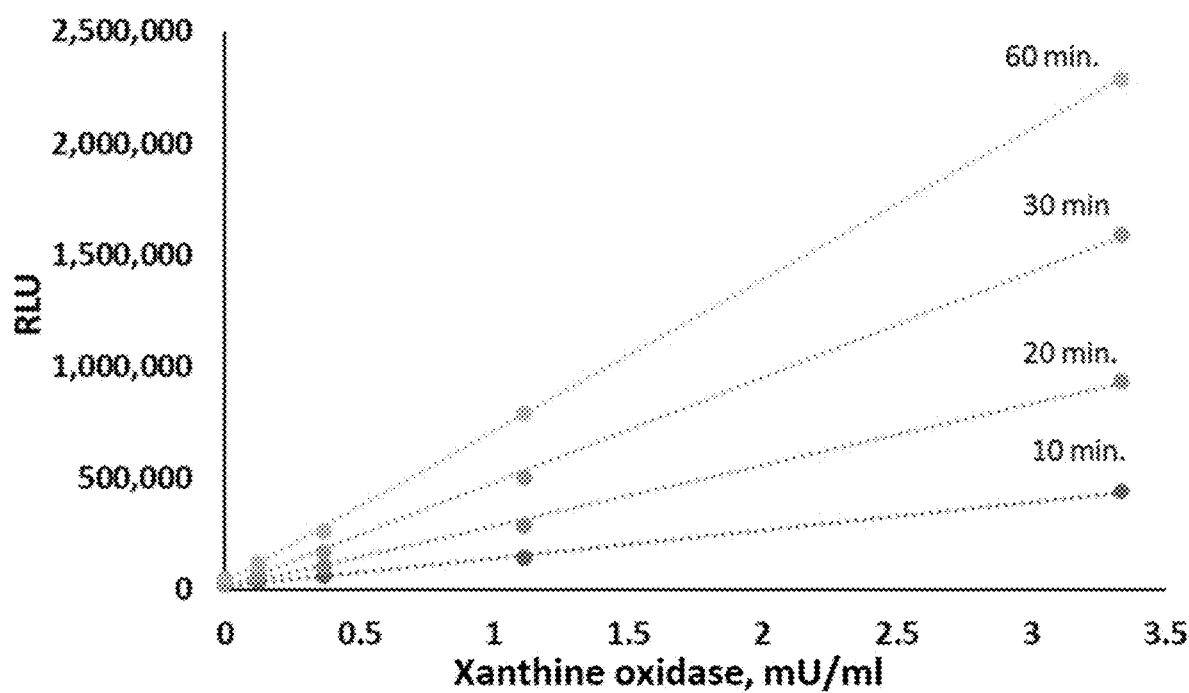
FIG. 5 shows data from assays to detect xanthine oxidase (XO) activity in vitro as described in Example 4.

The increase in luminescence signal depended on the presence of the xanthine oxidase substrate, xanthine, and was linear with respect to xanthine oxidase concentration and time. The data shown in FIG. 5 demonstrates that superoxide produced by xanthine oxidase interacts with pro-luciferin compound to release luciferin and can be used for measuring activity or inhibitor screening for superoxide producing enzymes.

Example 5: Detection of Superoxide Production by Macrophages

Production of superoxide by macrophages plays an important role in immune response and inflammation. Superoxide is produced by nicotinamide adenine dinucleotide phosphate (NADPH) oxidases (known as NOX enzymes) and is induced by PMA (4β-phorbol-12-myristate-13-acetate). Here is shown an example of measuring PMA-induced superoxide production in RAW 247.6 macrophage cell line. RAW 247.6 cells were plated overnight in DMEM medium with 10% FBS. To start the experiment, the medium was removed, cells were washed once with PBS, and 50 µl of PBS containing 5 mM glucose, 1 mM $MgCl_2$, 0.5 mM $CaCl_2$, and 0.05% BSA was added to the cells in the presence or absence of 20 µM PMA. To measure production of superoxide, 50 µl of 50 µM Compound 18 (FIG. 6A) or 100 µM Compound 20 (FIG. 6B) was added to the cells. Cells were treated for 2 hours at 37° C. with luciferin production measured by adding equal volume of Luciferin Detection Reagent with esterases, and luminescence read after 20 minutes incubation at room temperature.

With both compounds, higher luminescence signal was measured in the presence of cells as compared to medium only control. The data in FIGS. 6A-6B shows that luminescence signal increased significantly with PMA treatment illustrating the utility of the invented method to measure drug induced changes in superoxide production by mammalian cells.

Example 6: Detection of Superoxide Production in Kinetic Mode

Figure 7:
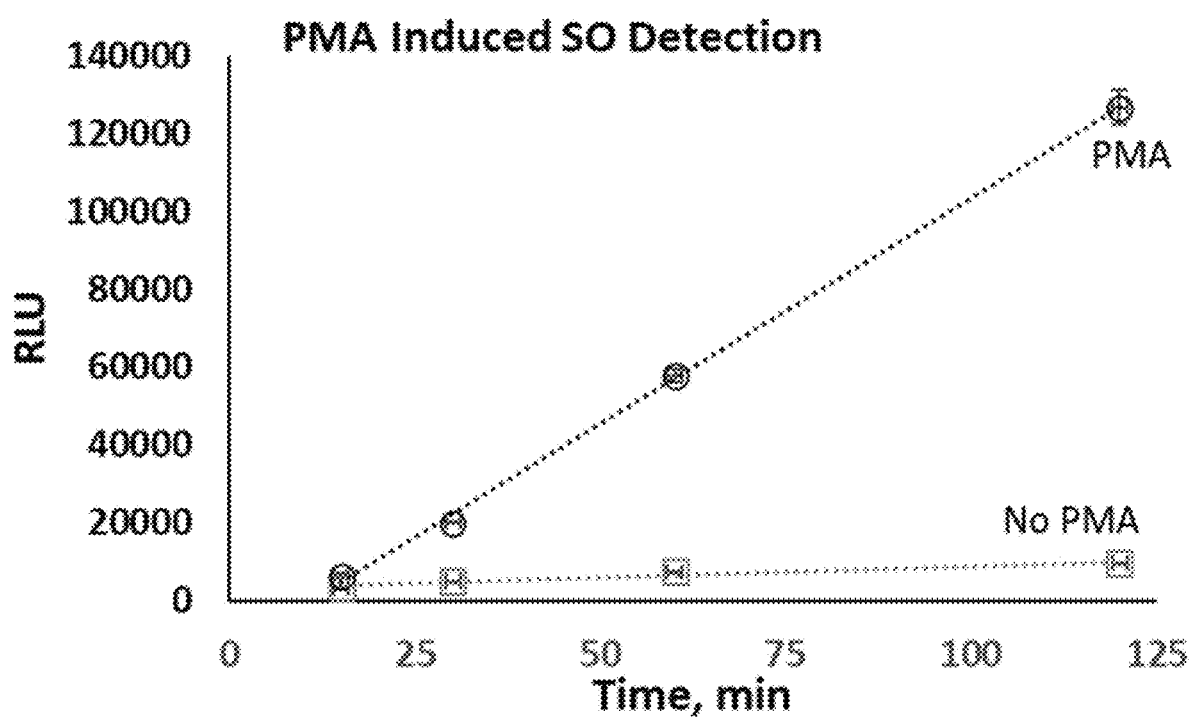
FIG. 7 shows data from assays to detect superoxide production in kinetic mode as described in Example 6.

RAW 247.6 macrophage cells were plated at 30,000 cells per well overnight in DMEM medium with 10% FBS. The following day, the medium was removed, and cells were washed with PBS. 100 µl PBS containing 5 mM glucose, 1 mM $MgCl_2$, 0.5mM $CaCl_2$, 0.05% BSA, and 50 µM Compound 20 were added to the cells in the presence or absence of 20 µM PMA. The cells were placed back at 37° C. in tissue culture incubator. At different time points (10, 20, 30 and 60 minutes), 10 µl was removed from the samples, mixed with 10 µl of Luciferin Detection Reagent with esterases, and luminescence read following a 20 minute incubation at room temperature. The data in FIG. 7 shows a time dependent increase in signal was detected in cells treated with PMA indicating increase in superoxide production.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (II):

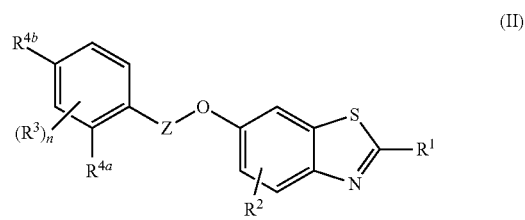

or a salt thereof, wherein:

$R^1$ is selected from —CN and

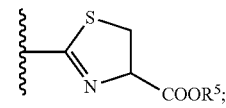

$R^2$ is selected from hydrogen and halo;

n is 0, 1, 2, or 3; and each $R^3$ is independently selected from $C_1$-$C_4$ alkyl, $C_1$-$C_4$ alkoxy, —OC(O)-$C_1$-$C_4$ alkyl, hydroxy, amino, and a group -Linker-X, wherein X is a targeting moiety;

one of $R^{4a}$ and $R^{4b}$ is hydroxy or —OC(O)-$C_1$-$C_4$ alkyl, and the other is hydrogen or a group -Linker-X, wherein X is a targeting moiety;

$R^5$ is selected from hydrogen and $C_1$-$C_4$ alkyl;

Z is a bond or a group of formula

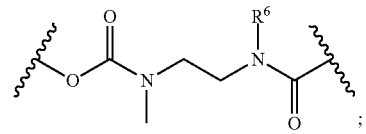

and $R^6$ is selected from $C_1$-$C_4$ alkyl and a group -Linker-Y, wherein Y is a targeting moiety.

2. The compound of claim 1, or a salt thereof, wherein Z is a group of formula

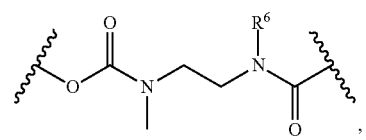

wherein $R^6$ is methyl or a group -Linker-Y, wherein Y is a mitochondrial targeting moiety.

3. The compound of claim 2, or a salt thereof, wherein Y is a triphenylphosphonium moiety.

4. The compound of claim 1, wherein the compound is a compound of formula (I):

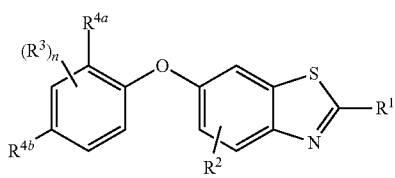

or a salt thereof, wherein:
$R^1$ is selected from —CN and

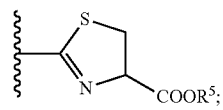

$R^2$ is selected from hydrogen and halo;
n is 0, 1, 2, or 3; and
each $R^3$ is independently selected from $C_1$-$C_4$ alkyl, $C_1$-$C_4$ alkoxy, amino, and a group -Linker-X, wherein X is a targeting moiety;
one of $R^{4a}$ and $R^{4b}$ is hydroxy and the other is hydrogen or a group -Linker-X, wherein X is a targeting moiety; and
$R^5$ is selected from hydrogen and $C_1$-$C_4$ alkyl.

5. The compound of claim 1, or a salt thereof, wherein $R^1$ is —CN.

6. The compound of claim 1, or a salt thereof, wherein $R^1$ is

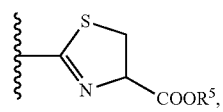

wherein $R^5$ is selected from hydrogen and methyl.

7. The compound of claim 1, or a salt thereof, wherein $R^2$ is hydrogen or fluoro.

8. The compound of claim 1, or a salt thereof, wherein the compound is a compound of formula (Ia):

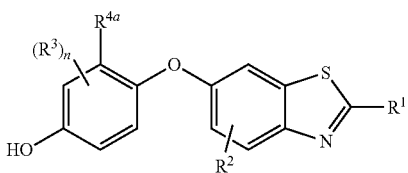

or a salt thereof, wherein $R^{4a}$ is hydrogen or a group -Linker-X, wherein X is a targeting moiety.

9. The compound of claim 1, or a salt thereof, wherein the compound is a compound of formula (Ib):

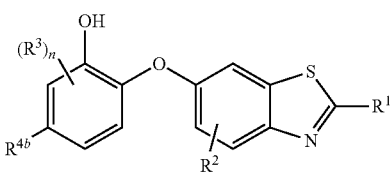

or a salt thereof, wherein $R^{4b}$ is hydrogen or a group -Linker-X, wherein X is a targeting moiety.

10. The compound of claim 1, or a salt thereof, wherein n is 0, 1, or 2, and each $R^3$ is independently selected from $C_1$-$C_4$ alkyl, $C_1$-$C_4$ alkoxy, —OC(O)-$C_1$-$C_4$ alkyl, and hydroxy.

11. The compound of claim 1, or a salt thereof, wherein at least one $R^3$ is a group -Linker-X, wherein X is a mitochondrial targeting moiety.

12. The compound of claim 11, or a salt thereof, wherein X is a triphenylphosphonium moiety.

13. The compound of claim 1, selected from the group consisting of:

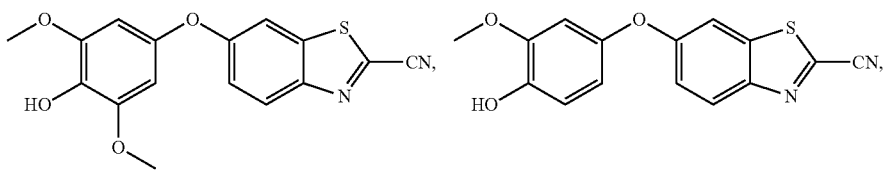

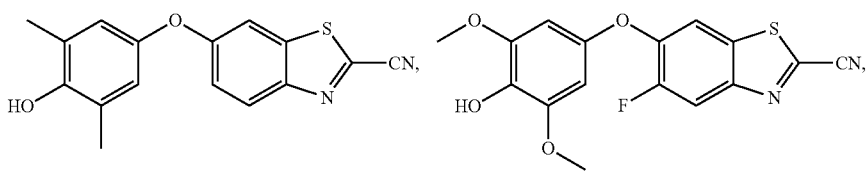

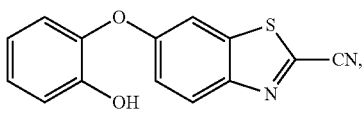

-continued
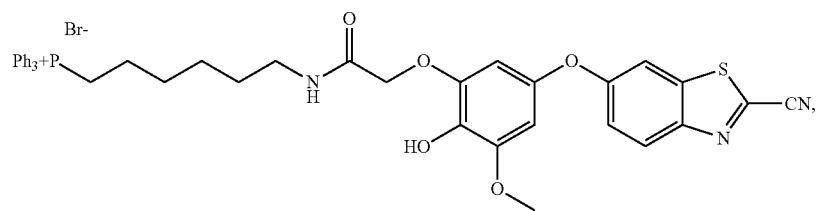
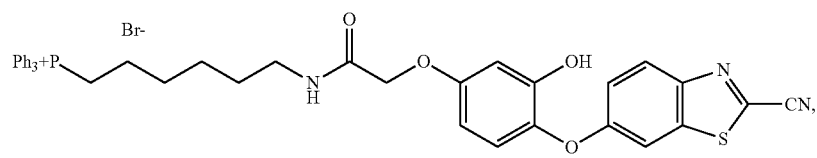
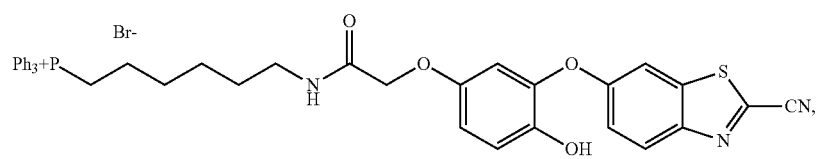
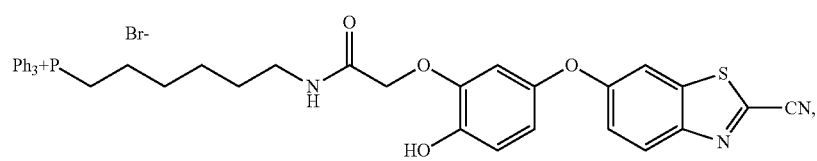
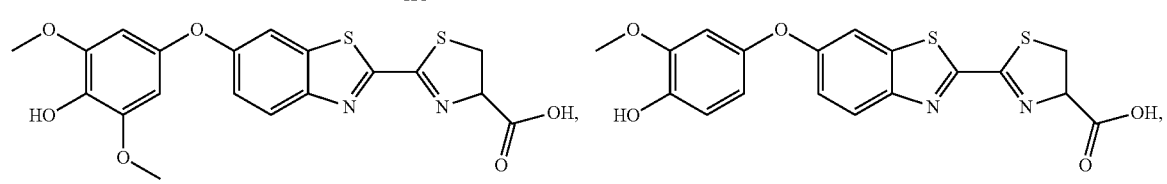
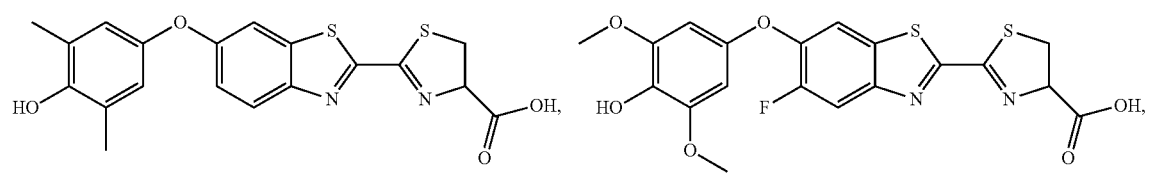
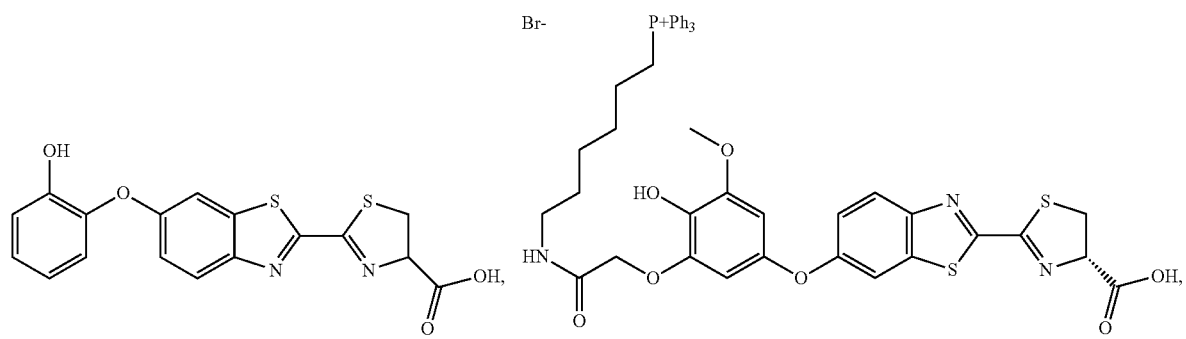
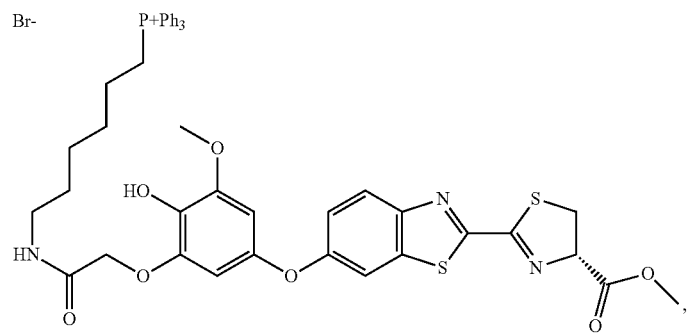

-continued
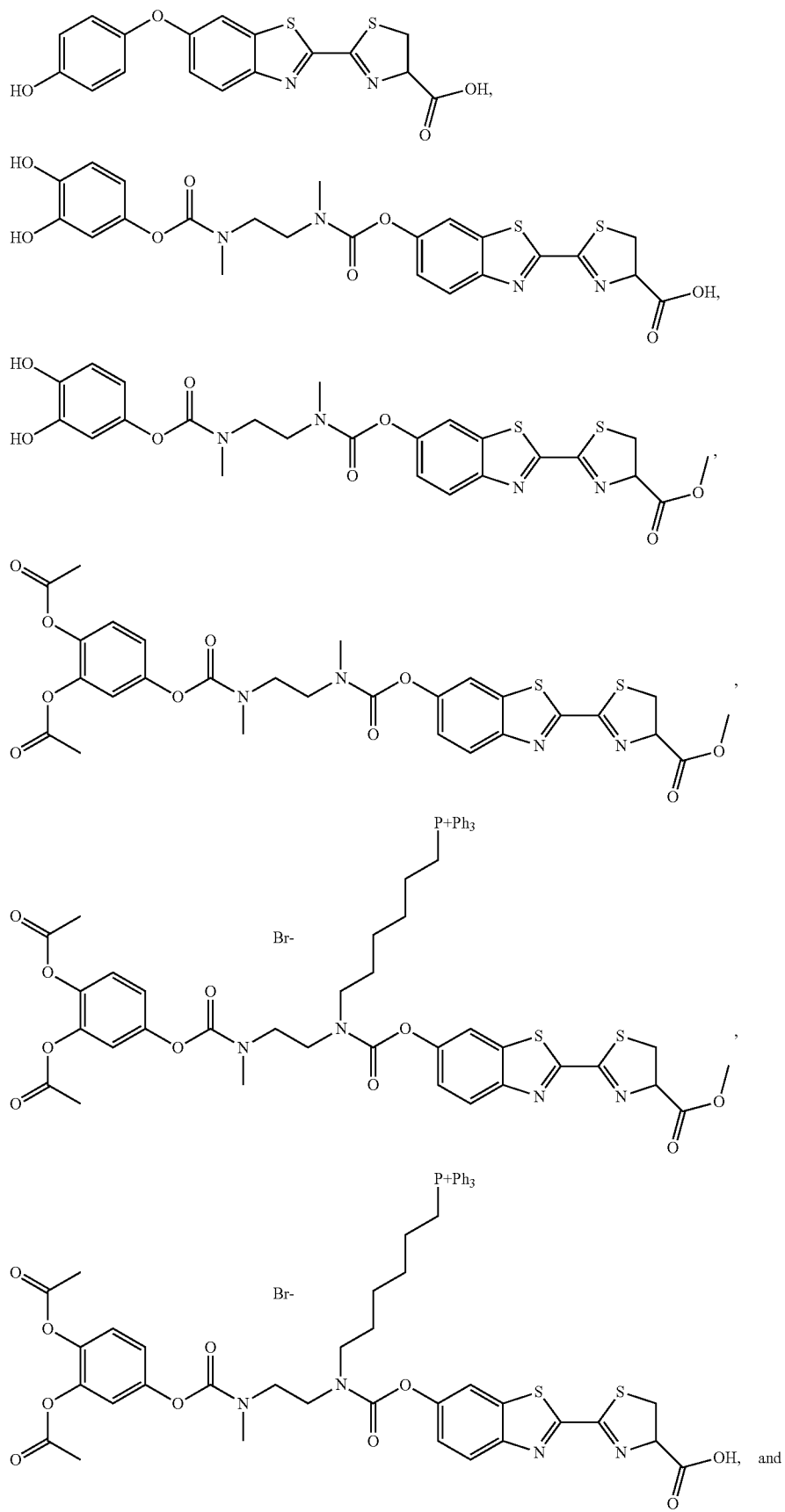

-continued

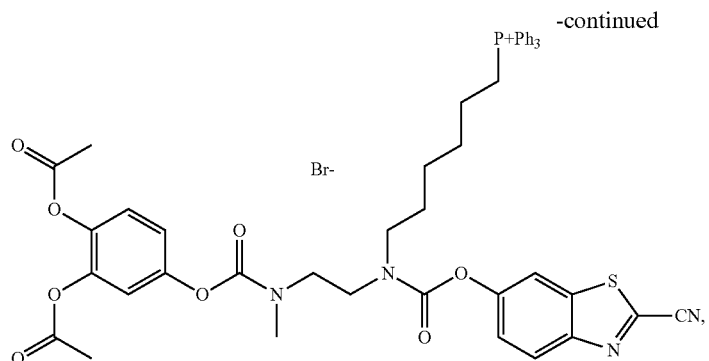

or a salt thereof.

14. A method of detecting superoxide in a sample, comprising:
    contacting the sample with a compound claim 1, or a salt thereof;
    contacting the sample with a luciferin-utilizing luciferase, if it is not already present in the sample; and
    detecting luminescence in the sample.

15. The method of claim 14, wherein the sample comprises live cells.

16. The method of claim 15, wherein the cells express the luciferin-utilizing luciferase.

17. The method of claim 14, comprising adding the luciferin-utilizing luciferase to the sample.

18. The method of claim 14, wherein the luciferin-utilizing luciferase is a firefly luciferase or a click beetle luciferase.

19. A kit comprising a compound of claim 1, or a salt thereof.

20. The kit of claim 19, further comprising a luciferin-utilizing luciferase enzyme, a nucleotide sequence encoding a luciferin-utilizing luciferase enzyme, or a buffer reagent.

* * * * *